(12) United States Patent
Nakamura et al.

(10) Patent No.: US 10,397,496 B2
(45) Date of Patent: Aug. 27, 2019

(54) IMAGING DEVICE PROVIDED WITH LIGHT SOURCE, IMAGE SENSOR INCLUDING FIRST ACCUMULATOR AND SECOND ACCUMULATOR, AND CONTROLLER

(71) Applicant: Panasonic Intellectual Property Management Co., Ltd., Osaka (JP)

(72) Inventors: Tatsuya Nakamura, Osaka (JP); Toshiya Fujii, Shiga (JP); Masaaki Yanagida, Kyoto (JP); Takamasa Ando, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 156 days.

(21) Appl. No.: 15/610,675

(22) Filed: Jun. 1, 2017

(65) Prior Publication Data
US 2017/0353672 A1    Dec. 7, 2017

(30) Foreign Application Priority Data
Jun. 7, 2016    (JP) .................. 2016-113424

(51) Int. Cl.
  *H04N 7/18*    (2006.01)
  *H04N 5/33*    (2006.01)
  (Continued)

(52) U.S. Cl.
  CPC .................. *H04N 5/33* (2013.01); *A61B 1/04* (2013.01); *A61B 1/06* (2013.01); *A61B 5/0042* (2013.01);
  (Continued)

(58) Field of Classification Search
  CPC ...... H04N 5/33; H04N 5/2354; H04N 5/2256; H04N 5/361; A61B 5/4064;
  (Continued)

(56) References Cited

U.S. PATENT DOCUMENTS

| 5,305,759 | A | 4/1994 | Kaneko et al. |
| 2008/0122933 | A1 | 5/2008 | Murayama |

(Continued)

FOREIGN PATENT DOCUMENTS

| JP | 4-189349 | 7/1992 |
| JP | 5-261107 | 10/1993 |

(Continued)

*Primary Examiner* — Richard T Torrente
(74) *Attorney, Agent, or Firm* — McDermott Will & Emery LLP

(57) ABSTRACT

An imaging device includes a light source, an image sensor, and a controller. Each pixel of the image sensor includes first and second accumulators and a discharger. The controller, while a component of light from the light source reflected by the surface of a target is incident on the image sensor, causes the accumulators to accumulate signal charge not discharged to the discharger, by setting the image sensor so that signal charge is discharged to the discharger, while a component having scattered inside the target is incident on the image sensor, causes the first accumulator to accumulate signal charge by setting the image sensor so that signal charge is not discharged to the discharger and signal charge is accumulated in the first accumulator, and causes the image sensor to generate first and second signals that are respectively based on signal charge accumulated in the first and second accumulators.

13 Claims, 25 Drawing Sheets

(51) Int. Cl.
    *A61B 1/04*     (2006.01)
    *A61B 1/06*     (2006.01)
    *G06T 7/20*     (2017.01)
    *G06T 11/60*     (2006.01)
    *H04N 5/225*     (2006.01)
    *A61B 5/00*     (2006.01)
    *A61B 5/1455*     (2006.01)
    *H04N 5/235*     (2006.01)
    *A61B 5/026*     (2006.01)
    *G06T 7/00*     (2017.01)
    *H04N 5/361*     (2011.01)
    *A61B 5/021*     (2006.01)
    *A61B 5/024*     (2006.01)
    *A61B 5/145*     (2006.01)
    *A61B 5/16*     (2006.01)

(52) U.S. Cl.
    CPC ........ *A61B 5/1455* (2013.01); *A61B 5/14553* (2013.01); *A61B 5/4064* (2013.01); *A61B 5/7207* (2013.01); *G06T 7/20* (2013.01); *G06T 11/60* (2013.01); *H04N 5/2256* (2013.01); *H04N 5/2354* (2013.01); *A61B 5/021* (2013.01); *A61B 5/0261* (2013.01); *A61B 5/02416* (2013.01); *A61B 5/14546* (2013.01); *A61B 5/165* (2013.01); *G06T 7/0012* (2013.01); *G06T 2207/10048* (2013.01); *G06T 2207/20224* (2013.01); *H04N 5/361* (2013.01)

(58) Field of Classification Search
    CPC . A61B 5/14553; A61B 5/1455; A61B 5/0042; A61B 5/7207; A61B 1/04; A61B 1/06; A61B 5/14546; A61B 5/02416; A61B 5/021; A61B 5/165; A61B 5/0261; G06T 11/60; G06T 7/20; G06T 7/0012; G06T 2207/10048; G06T 2207/20224
    See application file for complete search history.

(56) References Cited

U.S. PATENT DOCUMENTS

2010/0201797 A1*   8/2010   Shizukuishi ........... A61B 1/045
                                                         348/68
2015/0173618 A1    6/2015   Kusukame

FOREIGN PATENT DOCUMENTS

| JP | 2007-259987 | 10/2007 |
| --- | --- | --- |
| JP | 2008-008700 | 1/2008 |
| JP | 2012-134756 | 7/2012 |
| JP | 2015-134157 | 7/2015 |

* cited by examiner

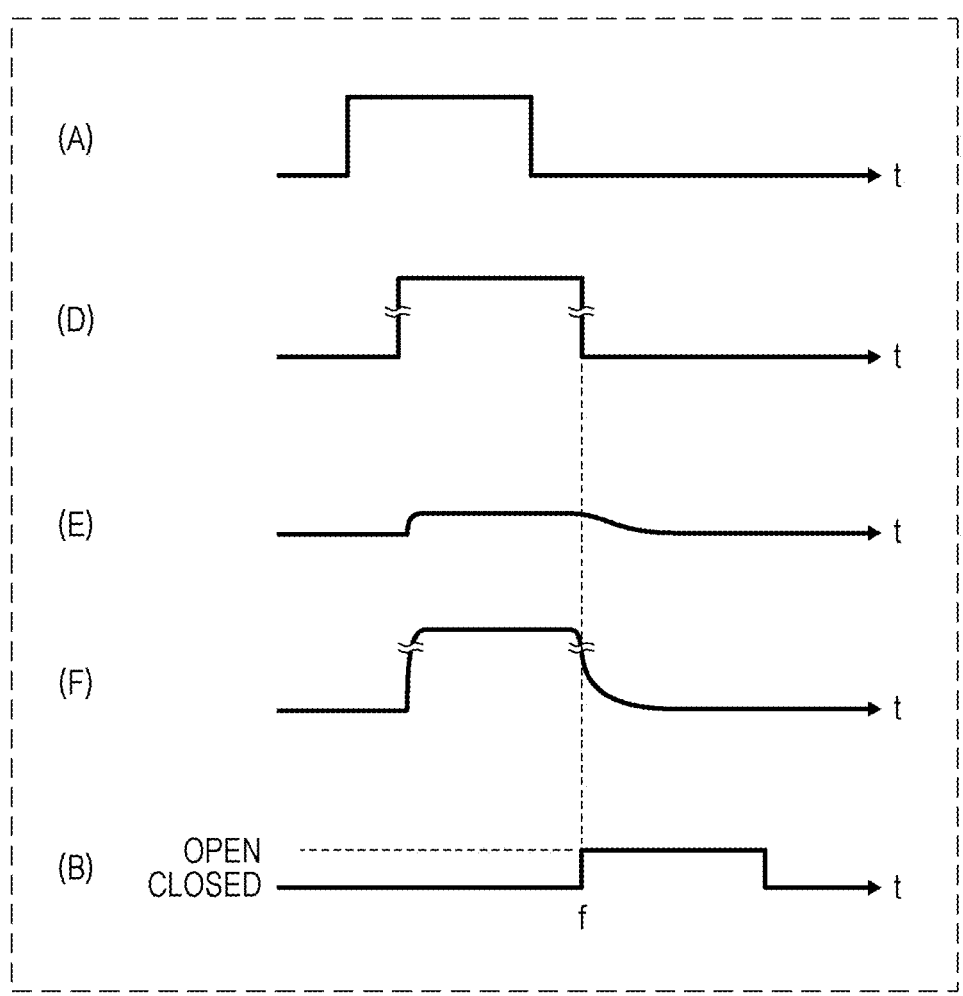

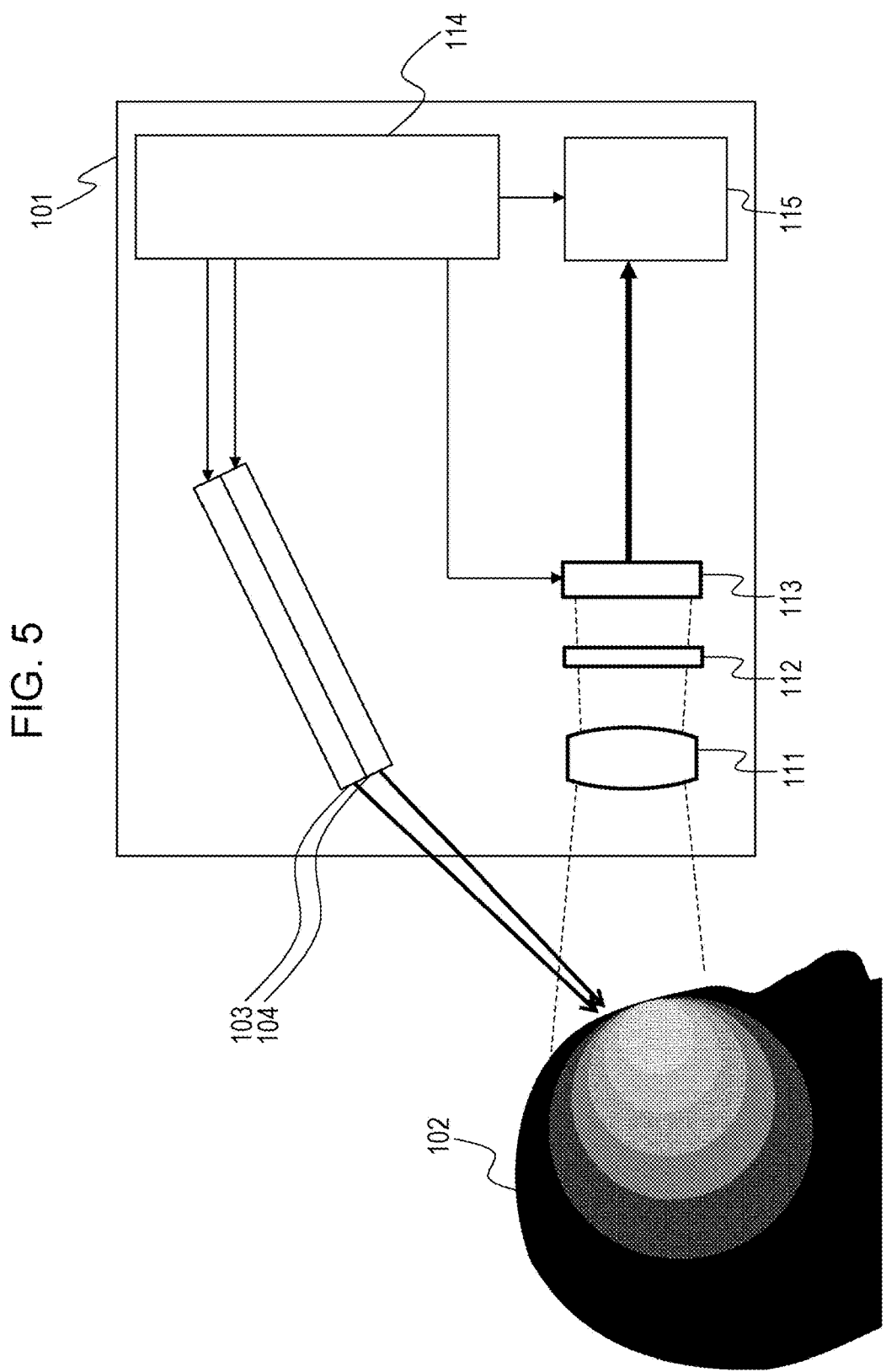

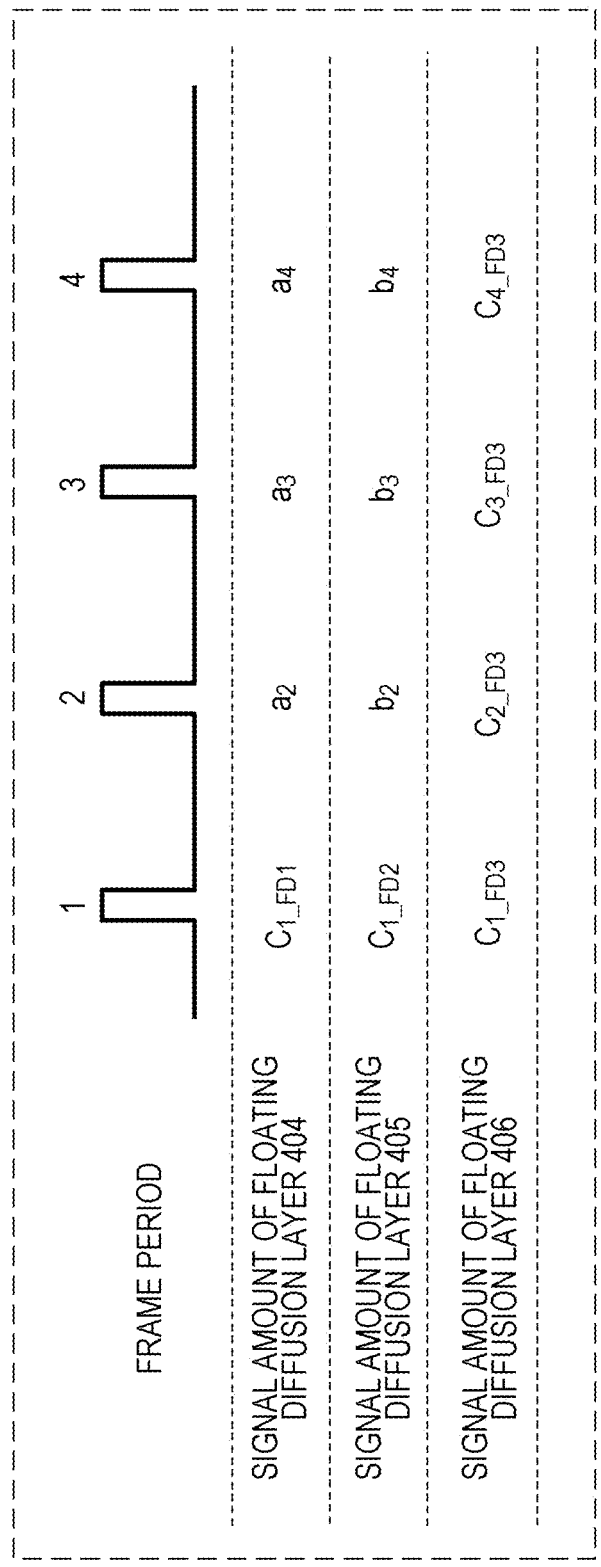

FIG. 15

| FRAME PERIOD | n | n+1 | n+2 | n+3 | n+4 | n+5 | n+6 | n+7 |
|---|---|---|---|---|---|---|---|---|
| SIGNAL READING | | | | | | | | |
| FD1 | $a_1$ | $b_2$ | $\boxed{c_3}$ | $a_4$ | $b_5$ | $c_6$ | $a_7$ | $b_8$ |
| FD2 | $b_1$ | $c_2$ | $a_3$ | $b_4$ | $c_5$ | $a_6$ | $b_7$ | $c_8$ |
| FD3 | $c_1$ | $a_2$ | $b_3$ | $c_4$ | $a_5$ | $b_6$ | $\boxed{c_7}$ | $a_8$ |
| FRAME MEMORY READING | | | | | | | | |
| FD1 | $c_0$ | $a_1$ | $b_2$ | $c_3$ | $a_4$ | $b_5$ | $\boxed{c_6}$ | $a_7$ |
| FD2 | $a_0$ | $b_1$ | $\boxed{c_2}$ | $a_3$ | $b_4$ | $c_5$ | $a_6$ | $b_7$ |
| FD3 | $b_0$ | $c_1$ | $a_2$ | $b_3$ | $c_4$ | $a_5$ | $b_6$ | $c_7$ |
| STATIONARY DETECTION/ COEFFICIENT WRITING | | | | STATIONARY | | | | STATIONARY |
| Read $\alpha$ | $\alpha_1$ | $\alpha_1$ | $\alpha_1$ | $\alpha_1$ | $\alpha_2$ | $\alpha_2$ | $\alpha_2$ | $\alpha_2$ |
| Read $\beta$ | $\beta_1$ | $\beta_1$ | $\beta_1$ | $\beta_1$ | $\beta_1$ | $\beta_1$ | $\beta_1$ | $\beta_1$ |
| write $\alpha$ | | | $\boxed{\alpha_2}$ | | | | | |
| write $\beta$ | | | ($\alpha_2 = C_2/C_3$) | | | | | $\boxed{\beta_2}$ |
|  | | | | | | | | ($\beta_2 = C_7/C_6$) |
| CORRECTION | | | | | | | | |
| FD1 | $a_1-c_1/\beta_1$ | $b_2-c_2/\alpha_1$ | $c_3$ | ... | | | | |
| FD2 | $b_1-c_1/\beta_1\cdot\alpha_1$ | $c_2$ | $a_3-c_3\cdot\alpha_1$ | ... | | | | |
| FD3 | $c_1$ | $a_2-c_2\cdot\beta_1/\alpha_1$ | $b_3-c_3\cdot\beta_1$ | ... | | | | |

IMAGING DEVICE PROVIDED WITH LIGHT SOURCE, IMAGE SENSOR INCLUDING FIRST ACCUMULATOR AND SECOND ACCUMULATOR, AND CONTROLLER

BACKGROUND

1. Technical Field

The present disclosure relates to an imaging device for acquiring internal information of a target object.

2. Description of the Related Art

In the fields of biometry and material analysis, methods are used in which light is radiated onto a target object, and internal information of the target object is acquired in a non-contact manner from the information regarding the light that has passed through the inside of the target object. For example, Japanese Unexamined Patent Application Publication No. 2015-134157 discloses a method in which the head of a person is irradiated with light, and light that has diffused inside the living body is detected using an image sensor such as a CMOS or CCD. Furthermore, Japanese Unexamined Patent Application Publication No. 4-189349 discloses a method in which information in different locations in the depth direction is detected using a streak camera.

SUMMARY

In one general aspect, the techniques disclosed here feature an imaging device for capturing an image of a target object, provided with: a first light source that, in operation, emits pulsed light that is radiated onto the target object; an image sensor that includes pixels, each of the pixels including a photoelectric conversion element that, in operation, converts incident light into signal charge, a first accumulator that, in operation, accumulates the signal charge, a second accumulator that, in operation, accumulates the signal charge, and a discharger that, in operation, discharges the signal charge; and a controller that, in operation, controls the first light source and the image sensor. The controller, in a first frame period that is a period in which the image of one frame is captured, causes the first light source to emit the pulsed light, in a first period that includes a period in which, from within the pulsed light, a surface reflected component reflected by a surface of the target object is incident on the image sensor, causes the first accumulator and the second accumulator to accumulate, from within the signal charge, a portion that has not been discharged to the discharger, by setting a state of the image sensor to a state in which the signal charge is discharged to the discharger, in a second period in which, from within the pulsed light, an internally scattered component that has scattered inside the target object is incident on the image sensor, causes the first accumulator to accumulate the signal charge by setting the state of the image sensor to a state in which the signal charge is not discharged to the discharger and the signal charge is accumulated in the first accumulator, and, after the first period and the second period, causes the image sensor to generate a first signal that is based on the signal charge accumulated in the first accumulator, and a second signal that is based on the signal charge accumulated in the second accumulator.

The aforementioned general or specific aspect may be realized by using a system, a method, an integrated circuit, a computer program, or a recording medium, or may be realized by using any combination of a system, a device, a method, an integrated circuit, a computer program, and a recording medium.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 is a drawing depicting the relationship between the timing at which light is emitted from a light source, the timing at which light from a target object is incident on the image sensor, and the timing of an electronic shutter;

FIG. 5 is a drawing schematically depicting a configuration of an imaging device in embodiment 1 of the present disclosure;

FIG. 12 is a drawing schematically depicting frame periods and signal amounts of each floating diffusion layer in embodiment 2;

FIG. 15 is a drawing for describing a specific example of signal processing in embodiment 3;

DETAILED DESCRIPTION (Findings Forming the Basis for the Present Disclosure)

The findings forming the basis for the present disclosure will be described prior to describing embodiments of the present disclosure.

According to the investigations of the present inventors, the aforementioned prior art was found to have the following problems.

In the method disclosed in Japanese Unexamined Patent Application Publication No. 2015-134157, most of the components included in the detected light are components of light reflected by the surface of the living body, and the components of light that have passed through inside the living body (for example, the brain) are minuscule in amount. Therefore, with respect to the signal amount afforded by the components of light that have passed through the brain, shot noise caused by the components of light reflected by the surface increases to an extent that cannot be ignored. In other words, there is a problem in that the signal-to-noise ratio (SN ratio) becomes low. However, in the method disclosed in Japanese Unexamined Patent Application Publication No. 4-189349, only one-dimensional information can be acquired regarding the spatial information of a target object. Furthermore, there is a problem in that this method is extremely expensive owing to the use of a streak camera and a light source of an ultrashort pulse having a pulse width of several hundred femtoseconds to several picoseconds.

Figure 1:
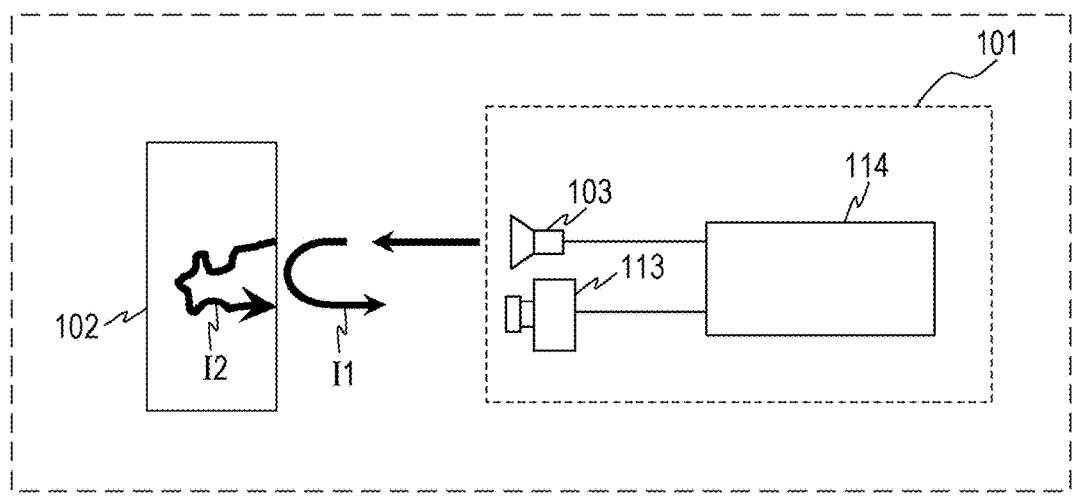
FIG. 1 is a schematic drawing depicting a schematic configuration of an imaging device.

The present inventors investigated an imaging device which is based on a principle that is different from that of the aforementioned prior art. FIG. 1 is a schematic drawing depicting a schematic configuration of such an imaging device. The present inventors attempted to measure a target object 102 (in this example, cerebral blood flow inside the head of a person's body) in a non-contact manner using an imaging device 101 (also referred to as a "time-resolved imaging system") such as that depicted in FIG. 1. This imaging device 101 is provided with: a first light source 103 that emits pulsed light of the near-infrared region; an image sensor 113 that detects pulsed light emitted from the first light source 103 and returned from the target object 102; and a control circuit 114 that controls the first light source 103 and the image sensor 113.

The first light source 103 is a laser pulse light source, for example, and repeatedly emits short-pulse light having a wavelength of the near-infrared region, in a high-speed pattern determined by the control circuit 114. In the case where the detection target is a living body, the wavelength of the light emitted from the first light source 103 may be set to approximately 650 nm or more to approximately 950 nm or less, for example. This wavelength range is included in the wavelength range from the red color to near-infrared rays, has a low absorption rate inside a living body, and is suitable for use in acquiring information regarding inside a living body. In the present specification, it should be noted that the term "light" is used for not only visible light but also infrared rays, and that infrared rays are sometimes referred to as "infrared light".

The image sensor 113 has a high temporal resolution with which it is possible to control the accumulation and emission of signals at a time scale of picoseconds to nanoseconds, for example. The control circuit 114 controls the light emission timing of the first light source 103 and the exposure timing of each pixel of the image sensor 113.

When light is radiated onto the target object 102 (for example, the forehead of the person), strong light l1 (sometimes referred to as "surface reflected light" or a "surface reflected component" hereinafter) reflected by the outermost surface layer of the target object 102 reaches the image sensor 113 first. Next, weak light l2 (sometimes referred to as "internally scattered light" or an "internally scattered component" hereinafter) that is scattered inside the target object 102 and returned reaches the image sensor 113 after the light l1. Information regarding the cerebral blood flow is reflected in the internally scattered component l2, and therefore the surface reflected component l1 is not required. Thus, the present inventors attempted to detect only the light l2 scattered inside the target object 102 using a time-resolved method.

Hereinafter, an example (study example) of a method in which the surface reflected component l1 and the internally scattered component l2 from the target object 102 are separated and detected will be described with reference to FIGS. 2 to 4.

Figure 2:
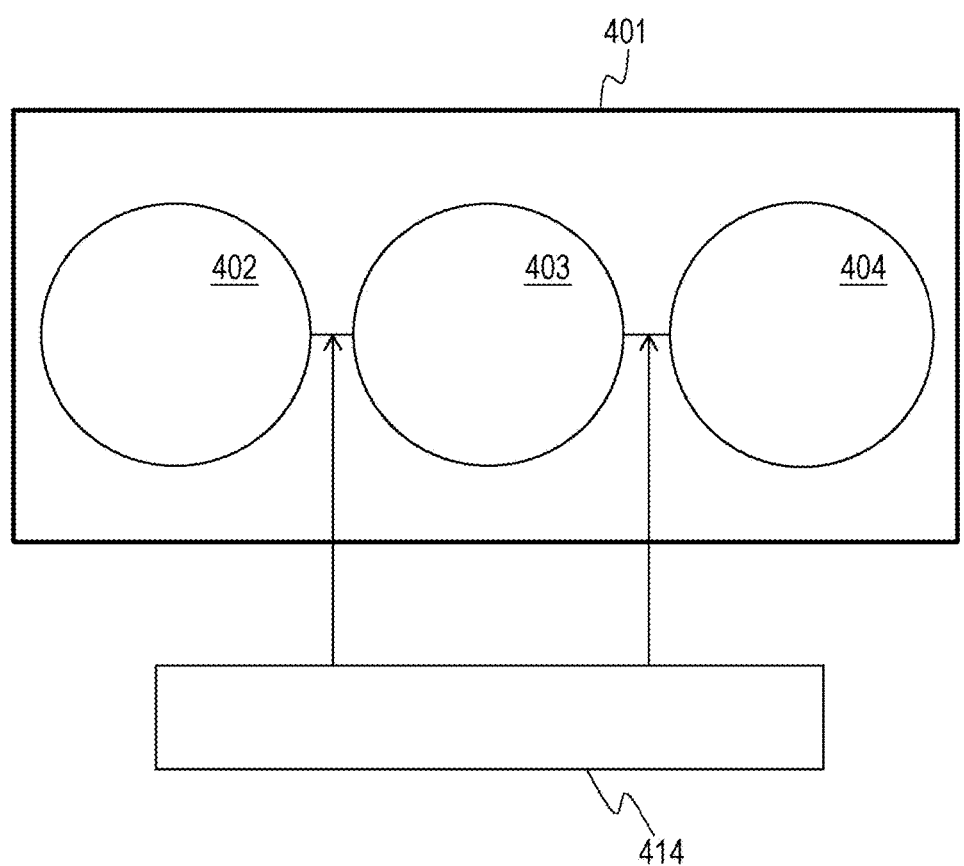
FIG. 2 is a drawing depicting a configuration of one pixel in an image sensor in a study example in a simple manner.

FIG. 2 is a diagram depicting a configuration of one pixel 401 in the image sensor 113 in a simple manner. The image sensor 113 has a plurality of pixels arrayed two-dimensionally on an imaging surface, and a high-speed timing control circuit 414 that controls the accumulation and discharge timings of signal charge of each pixel. The high-speed timing control circuit 414 operates on the basis of commands from the control circuit 114.

Each of the pixels 401 of the image sensor 113 includes: a photodiode 403 that is a photoelectric conversion element; a floating diffusion (FD) layer 404 that is an accumulation unit for accumulating signal charge; and a drain 402 that is a discharge unit for discharging signal charge.

Light that is incident on each of the pixels 401 due to one emission of pulsed light is converted by the photodiode 403 into signal electrons that constitute signal charge. The converted signal electrons are either discharged to the drain 402 or allocated to the floating diffusion layer 404 that accumulates signal charge, in accordance with a control signal that is input from the high-speed timing control circuit 414. An electronic shutter is realized by this control performed by the high-speed timing control circuit 414.

FIG. 3 is a drawing depicting the relationship between the timing at which light is emitted from the first light source 103, the timing at which light from the target object 102 is incident on the image sensor 113, and the timing of the electronic shutter. In FIG. 3, signal A indicates the waveform of pulsed light emitted from the first light source 103. Signal D indicates, from within the pulsed light, the waveform of the surface reflected component l1 that is reflected by the surface of the target object 102 and returned. Signal E indicates, from within the pulsed light, the waveform of the internally scattered component l2 that is scattered inside the target object 102 and returned. Signal F indicates a waveform in which the surface reflected component l1 and the internally scattered component l2 are combined. Signal B indicates the opening and closing timings of the electronic shutter. The horizontal axis indicates time, and the vertical axis indicates the intensity of light in signals A, D, E, and F, and the open or closed state of the electronic shutter in signal B. Here, "closed" refers to a state in which signal charge is discharged to the drain 402, and "open" refers to a state in which signal charge is not discharged. The high-speed timing control circuit 414 can control the accumulation of signal charge to the floating diffusion layer 404 and the discharge of signal charge to the drain 402, by changing the potential energy (simply referred to as "potential" hereinafter) of the signal charge in the floating diffusion layer 404 and the drain 402 by means of a voltage adjustment, for example.

When the first light source 103 radiates pulsed light onto the target object 102, the surface reflected component l1 and the internally scattered component l2 are generated, as previously mentioned. The internally scattered component l2 is light that has passed through inside the target object 102, and therefore has a long optical path length compared to the surface reflected component l1. Consequently, the internally scattered component l2 reaches the image sensor 113 after the surface reflected component l1. The high-speed timing control circuit 414 closes the electronic shutter while the surface reflected component l1 is incident on the image sensor 113. For example, the high-speed timing control circuit 414 increases the voltage applied to the drain 402 to lower the potential of the signal charge (electrons) in the drain 402 so that signal charge is discharged to the drain 402. When the incidence of the surface reflected component l1 on the image sensor 113 ends (time f in FIG. 3), the high-speed timing control circuit 414 opens the electronic shutter. For example, the high-speed timing control circuit 414 lowers the voltage applied to the drain 402 to increase the potential of the signal charge in the drain 402 so that signal charge is accumulated in the floating diffusion layer 404. Thereafter, the open state is maintained until a predetermined time elapses (for example, a time corresponding to the light-emission pulse width). During this time, signal charge caused by the internally scattered component l2 is accumulated in the floating diffusion (FD) layer 404. Thereafter, the high-speed timing control circuit 414 once again closes the electronic shutter. The control circuit 114 once again starts the emission of pulsed light after a predetermined time has elapsed from the electronic shutter being closed. Thereafter, the above operation is repeated a plurality of times (approximately several hundred times to several ten thousand times, for example). During that time, one frame image is generated on the basis of the signal charge accumulated in the floating diffusion layer 404.

In the present device, when the electronic shutter is closed (drain discharge is active, in other words), signal charge caused by the surface reflected component l1 is discharged to the drain 402. On the other hand, when the electronic shutter is open (drain discharge is inactive, in other words), signal charge caused by the internally scattered component l2 is accumulated in the FD 404. The potential of the signal charge in the photodiode 403, the FD 404, and the drain 402 in each of the pixels is designed in such a way that this kind of operation is realized. However, according to the investigations of the present inventors, even when the drain discharge is active, not all of the signal charge is actually discharged, and a small portion (for example, approximately one ten-thousandth) of the charge leaks into the FD 404. It was found that such leakage becomes considerable noise when detecting a weak biological signal such as cerebral blood flow, and leads to a decline in detection accuracy.

Hereinafter, this problem will be described in detail with reference to FIGS. 4A to 4D.

Figure 4A:
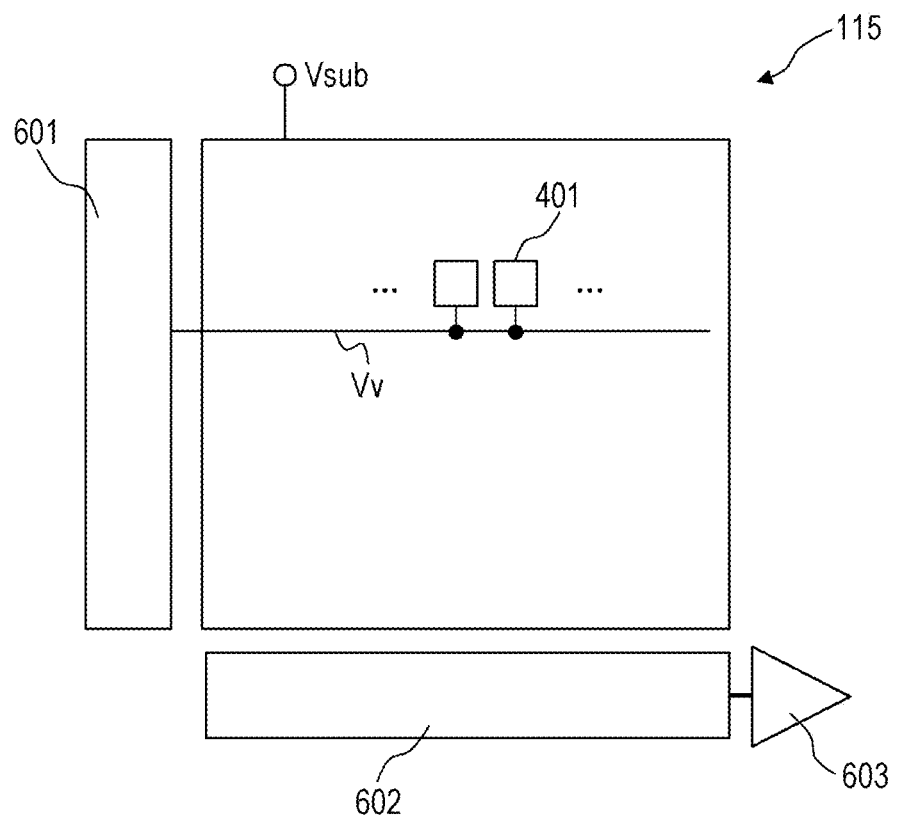
FIG. 4A is a drawing schematically depicting a configuration example of the image sensor.

FIG. 4A is a drawing schematically depicting a configuration example of the image sensor 113. Here, an image sensor 113 having a charge-coupled device (CCD) structure is considered as an example. This image sensor 113 is provided with: a pixel array in which a plurality of pixels 401 are arrayed two-dimensionally on an imaging surface; a pixel driving circuit 601; a horizontal CCD 602; and an output circuit 603.

Figure 4B:
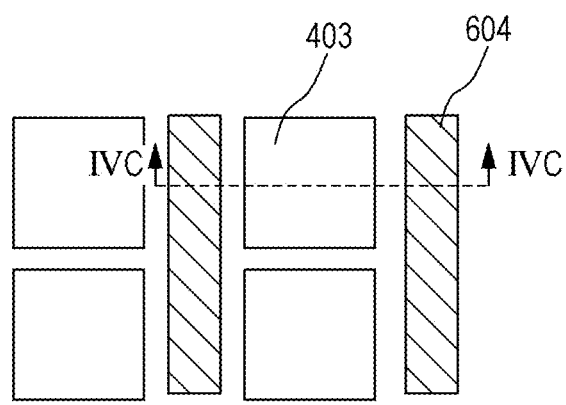
FIG. 4B is a drawing schematically depicting four adjacent pixels from within a pixel array.

FIG. 4B is a drawing schematically depicting four adjacent pixels from within the pixel array. One pixel 401 includes a photodiode 403. Vertical CCDs 604 are arranged adjacent to a plurality of photodiodes 403 arranged in the vertical direction (longitudinal direction in the drawing). A vertical CCD 604 is an element that perform the accumulation and transfer of signal charge, and corresponds to the FD 404 in FIG. 2.

Figure 4C:
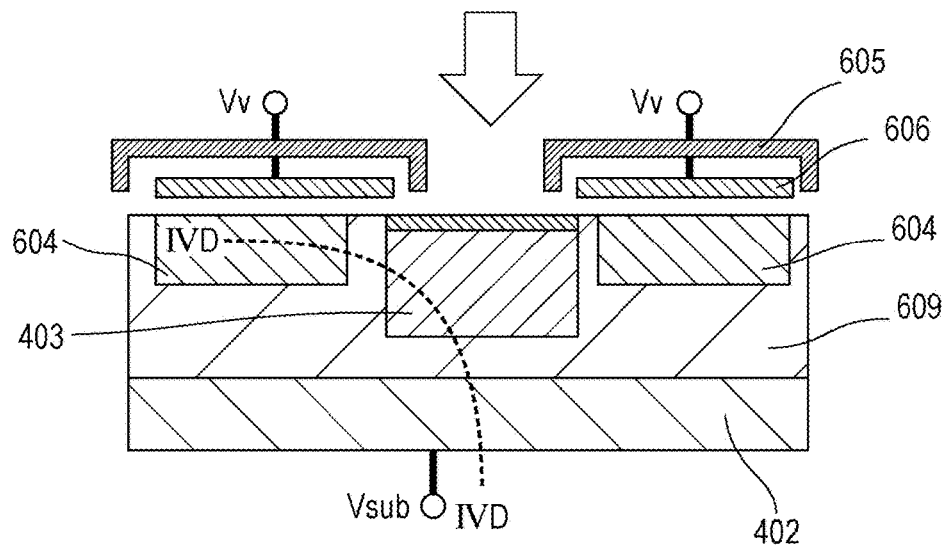
FIG. 4C is a drawing schematically depicting a cross section along the IVC-IVC line in FIG. 4B.

FIG. 4C is a drawing schematically depicting a cross section along the IVC-IVC line in FIG. 4B. As depicted in FIG. 4C, electrodes 606 and light-shielding members 605 that cover the electrodes 606 are provided above (front surface side) the vertical CCDs 604. An oxide film that is not depicted is present between the electrodes 606 and the vertical CCDs 604. The drain 402 is arranged on the rear surface side (the lower side in FIG. 4C) of the pixels. The drain 402 is a N-type semiconductor substrate, for example. A voltage Vv is applied to the vertical CCDs 604. A voltage Vsub is applied to the drain 402. The accumulation of signal charge to the vertical CCDs 604 and the discharge of signal charge are controlled by means of the voltage Vv and the voltage Vsub. The high-speed timing control circuit 414 controls signal accumulation and discharge timings by adjusting the voltages Vv and Vsub. A p-type well region 609 is arranged on the drain 402, for example. As depicted in FIG. 4C, the vertical CCDs 604 and the photodiode 403 are arranged inside the well region 609. The vertical CCDs 604 is an n-type semiconductor region, for example, and the photodiode 403 is configured of an n-type semiconductor region and a p-type semiconductor region arranged thereon, for example.

Figure 4D:
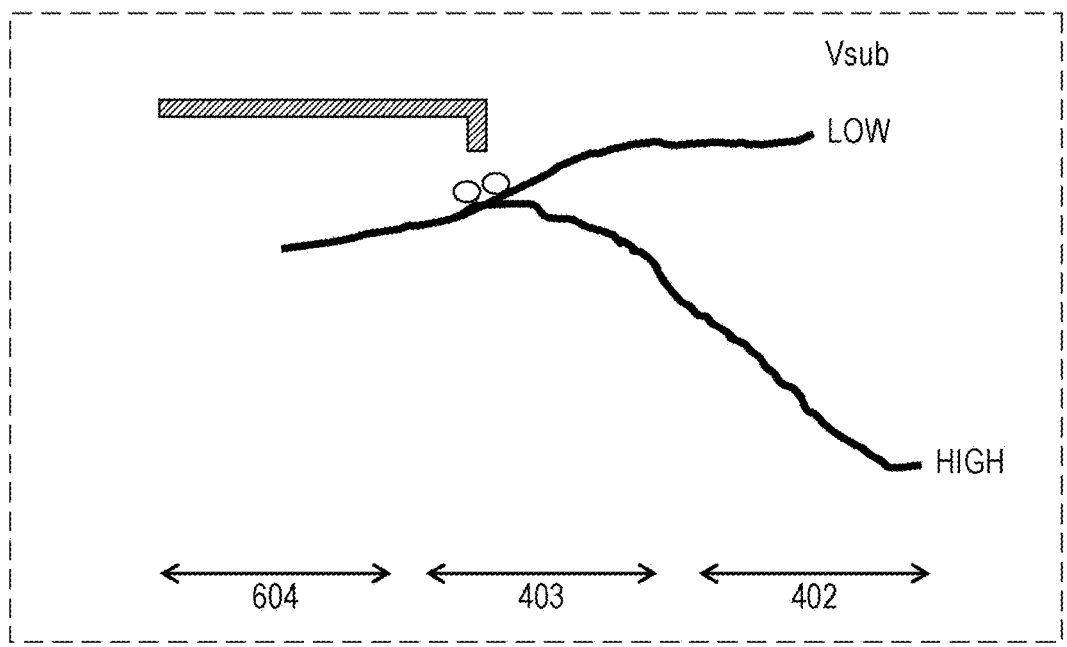
FIG. 4D is a drawing schematically depicting the potential of signal charge along the IVD-IVD line in FIG. 4C.

FIG. 4D is a drawing schematically depicting the potential of electrons constituting signal charge along the IVD-IVD line in FIG. 4C. In a state in which the voltage Vv is set to a certain value, when the voltage Vsub enters a low state that is lower than a predetermined value, the potential of the electrons in the drain 402 becomes higher than the potential in the vertical CCDs 604. In this state, signal charge is not discharged to the drain 402, and is accumulated in the vertical CCDs 604. This state corresponds to the electronic shutter being in an open state (the drain being inactive). However, when Vsub enters a high state that is higher than the aforementioned predetermined value, the potential of the electrons in the drain 402 becomes lower than the potential in the vertical CCDs 604. Therefore, signal charge is discharged to the drain 402. This state corresponds to the drain being in an active state in which the electronic shutter is in a closed state. In this state, the majority of signal charge is discharged to the drain 402, and signal charge is mostly not accumulated in the vertical CCDs 604. However, a small portion of signal charge (for example, approximately several ten-thousandths of the entirety) is not discharged to the drain 402, and is accumulated in the vertical CCDs 604. This is due to the peak potential of the signal charge being at the end section near the vertical CCDs 604, from within the region of the photodiode 403. Therefore, signal charge generated due to a portion of light (mainly oblique light) incident on the end section of the photodiode 403 may not be discharged to the drain 402, and may be accumulated in the vertical CCDs 604. Furthermore, there are cases where oblique light is directly incident on the vertical CCDs 604, and unnecessary signal charge is also accumulated in this case. The above problem is not restricted an image sensor having a CCD structure, and may likewise occur in also an image sensor having another structure such as a CMOS.

The signal charge photoelectrically converted when the electronic shutter is open and accumulated in the FD 404 or vertical CCD 604 constituting an accumulation unit is caused by the internally scattered component 12, and the amount thereof is approximately one ten-thousandth of the amount of signal charge caused by the surface reflected component 11, for example. Therefore, in the accumulation unit, the signal charge caused by the leakage of surface reflected light is intermixed at a ratio that cannot be ignored when compared to the signal charge caused by internally scattered light. In this kind of state, it is not possible to correctly detect the amount of internally scattered light or changes over time therein.

The above problem has not been recognized in conventional imaging devices. In the case where a general target object is captured using a conventional imaging device, the amount of light incident from the target object when the electronic shutter is in the open state is far greater than the amount of light that leaks into the accumulation unit when the electronic shutter is in an off state. Therefore, the leakage of light does not become a problem. However, in the case where weak biological information such as information regarding the cerebral blood flow inside a person's head is to be detected, the surface reflected component that leaks into the accumulation unit cannot be ignored with respect to the internally scattered component, and therefore the aforementioned problem occurs.

The present inventors discovered the above problem and investigated a configuration for a new image sensor. The present inventors found that by providing at least two signal accumulation units for each pixel of an image sensor, and using one of the signal accumulation units to detect components caused by the surface reflected light that leaks into the signal accumulation units, it is possible to eliminate unnecessary components from signals detected in the other signal accumulation unit. On the basis of the above consideration, the present inventors arrived at completing the imaging device described in the following items.

[Item 1]

An imaging device according to item 1 of the present disclosure is an imaging device for capturing an image of a target object, provided with:

a first light source that, in operation, emits pulsed light that is radiated onto the target object;

an image sensor that includes pixels, each of the pixels including a photoelectric converter that, in operation, converts incident light into signal charge, a first accumulator that, in operation, accumulates the signal charge, a second accumulator that, in operation, accumulates the signal charge, and a discharger that, in operation, discharges the signal charge; and a controller that, in operation, controls the first light source and the image sensor, in which the controller, in a first frame period that is a period in which the image of one frame is captured, causes the first light source to emit the pulsed light, in a first period that includes a period in which, from within the pulsed light, a surface reflected component reflected by a surface of the target object is incident on the image sensor, causes the first accumulator and the second accumulator to accumulate, from within the signal charge, a portion that has not been discharged to the discharger, by setting a state of the image sensor to a state in which the signal charge is discharged to the discharger, in a second period in which, from within the pulsed light, an internally scattered component that has scattered inside the target object is incident on the image sensor, causes the first accumulator to accumulate the signal charge by setting the state of the image sensor to a state in which the signal charge is not discharged to the discharger and the signal charge is accumulated in the first accumulator, and, after the first period and the second period, causes the image sensor to generate a first signal that is based on the signal charge accumulated in the first accumulator, and a second signal that is based on the signal charge accumulated in the second accumulator.

[Item 2]

In the imaging device according to item 1, a signal processor that is electrically connected to the image sensor may be further provided, and the signal processor may, in operation, generate a signal indicating the image, by performing a calculation using the first signal and the second signal, for each of the pixels.

[Item 3]

In the imaging device according to item 2, the signal processor may, in operation, generate the signal indicating the image, by subtracting the second signal from the first signal, for each of the pixels.

[Item 4]

In the imaging device according to item 1, the controller, in a second frame period that is different from the first frame period, may cause the first light source to emit the pulsed light, in a third period that includes a period in which, from within the pulsed light, the surface reflected component is incident on the image sensor, may cause the first accumulator and the second accumulator to accumulate, from within the signal charge, the portion that has not been discharged to the discharger, by setting the state of the image sensor to the state in which the signal charge is discharged to the discharger, and, after the third period, may cause the image sensor to generate a third signal that is based on the signal charge accumulated in the first accumulator, and a fourth signal that is based on the signal charge accumulated in the second accumulator.

[Item 5]

The imaging device according to item 4 may be further provided with a signal processor that is electrically connected to the image sensor, in which the signal processor may, in operation, generate a signal indicating the image, by performing a calculation using the first signal, the second signal, the third signal, and the fourth signal, for each of the pixels.

[Item 6]

In the imaging device according to item 5, when the first signal is S1, the second signal is S2, the third signal is S3, and the fourth signal is S4, the signal processor may, in operation, generate a signal S obtained by the calculation S=S1−S2×S3/S4, as the signal indicating the image.

[Item 7]

In the imaging device according to item 1, the controller, in a second frame period that is different from the first frame period, may cause the first light source to emit the pulsed light, in a third period that includes a period in which, from within the pulsed light, the surface reflected component is incident on the image sensor, may cause the first accumulator and the second accumulator to accumulate, from within the signal charge, the portion that has not been discharged to the discharger, by setting the state of the image sensor to the state in which the signal charge is discharged to the discharger, in a fourth period in which, from within the pulsed light, the internally scattered component is incident on the image sensor, may cause the second accumulator to accumulate the signal charge by setting the state of the image sensor to a state in which the signal charge is not discharged to the discharger and the signal charge is accumulated in the second accumulator, and, after the third period and the fourth period, may cause the image sensor to generate a third signal that is based on the signal charge accumulated in the first accumulator, and a fourth signal that is based on the signal charge accumulated in the second accumulator.

[Item 8]

In the imaging device according to item 7, a signal processor that is electrically connected to the image sensor may be further provided, and the signal processor may, in operation, generate a signal indicating the image in the second frame period, by subtracting a signal obtained by multiplying the third signal by a coefficient, from the fourth signal, for each of the pixels.

[Item 9]

In the imaging device according to item 8, the signal processor may, in operation, detect motion of the target object on the basis of the signal indicating the image, for each of the pixels, and may change the coefficient using at least one of the first to fourth signals, for a pixel in which no motion of the target object is detected, from among the pixels.

[Item 10]

In the imaging device according to item 1, the controller, in the first frame period, in a period in which the pulsed light is not incident on the image sensor, may cause the second accumulator to further accumulate the signal charge, by setting the state of the image sensor to a state in which the signal charge is not discharged to the discharger and the signal charge is accumulated in the second accumulator.

[Item 11]

In the imaging device according to item 1, the first light source may, in operation, emit first pulsed light and second pulsed light that is emitted after the first pulsed light, each of the first pulsed light and the second pulsed light being the pulsed light, and the controller, after incidence of the first pulsed light onto the image sensor has ended, before incidence of the second pulsed light onto the image sensor starts, may cause the second accumulator to further accumulate the signal charge, by setting the state of the image sensor to a state in which the signal charge is not discharged to the discharger and the signal charge is accumulated in the second accumulator.

[Item 12]

In the imaging device according to item 1, the controller, in the first frame period, after accumulation of signal charge caused by the pulsed light in the first and second accumulators has completed, may cause the second accumulator to further accumulate the signal charge, by setting the state of the image sensor to a state in which the signal charge is not discharged to the discharger and the signal charge is accumulated in the second accumulator.

[Item 13]

The imaging device according to any of items 1 to 12 may be further provided with a second light source that, in operation, emits third pulsed light that has a different wavelength from a wavelength of the pulsed light from the first light source, the image sensor may further include a third accumulator that, in operation, accumulates the signal charge, and the controller, in the first frame period, after the first period and the second period, may cause the second light source to emit the third pulsed light, in a fifth period that includes a period in which, from within the third pulsed light, the surface reflected component is incident on the image sensor, may cause the first accumulator, the second accumulator, and the third accumulator to accumulate, from within the signal charge, the portion that has not been discharged to the discharger, by setting the state of the image sensor to the state in which the signal charge is discharged to the discharger, in a sixth period in which, from within the third pulsed light, the internally scattered component is incident on the image sensor, may cause the third accumulator to accumulate the signal charge, by setting the state of the image sensor to a state in which the signal charge is not discharged to the discharger and the signal charge is accumulated in the third accumulator, and, after the fifth period and the sixth period, may cause the image sensor to generate the first signal that is based on the signal charge accumulated in the first accumulator, the second signal that is based on the signal charge accumulated in the second accumulator, and a third signal that is based on the signal charge accumulated in the third accumulator.

In the present disclosure, all or part of a circuit, unit, device, member or portion, or all or part of a functional block in the block diagrams may be implemented as one or more electronic circuits including a semiconductor device, a semiconductor integrated circuit (IC) or a large-scale integration (LSI). The LSI or IC may be integrated into one chip or may be configured as a combination of a plurality of chips. For example, functional blocks other than a storage element may be integrated into one chip. The name used here is LSI or IC, but it may also be called a system LSI, a very large scale integration (VLSI), or an ultra large scale integration (ULSI) depending on the degree of integration. A field programmable gate array (FPGA) that is programmed after manufacturing an LSI or a reconfigurable logic device that allows the reconfiguration of the connection relationship or the setup of circuit cells inside the LSI can be used for the same purpose.

Further, it is possible for all or part of the functions or operations of a circuit, unit, device, member, or portion to be executed by means of software processing. In such a case, software is recorded on one or more non-transitory recording media such as a ROM, an optical disk, or a hard disk drive, and when the software is executed by a processor, functions specified by the software are executed by the processor and peripheral devices. A system or device may be provided with one or more non-transitory recording media on which software is recorded, a processor, and necessary hardware devices such as an interface.

Hereinafter, embodiments of the present disclosure will be described in detail with reference to the drawings. It should be noted that the embodiments described hereinafter all represent general or specific examples. The numerical values, shapes, materials, constituent elements, arrangement and mode of connection of the constituent elements, steps, order of the steps, and the like given in the following embodiments are examples and are not intended to restrict the present disclosure. The various aspects described in the present specification can be combined with each other provided there are no resulting inconsistencies. Furthermore, from among the constituent elements in the following embodiments, constituent elements that are not mentioned in the independent claims indicating the most significant concepts are described as optional constituent elements. In the following description, constituent elements that are substantially the same or similar are denoted by common reference numerals, and descriptions thereof are sometimes omitted.

Embodiment 1

The imaging device of the present embodiment has, as a target object, a light scattering body such as a living body. More specifically, the imaging device of the present embodiment detects the concentration distribution of oxygenated hemoglobin and deoxygenated hemoglobin inside the brain of a subject to be observed, and changes over time therein. It is thereby possible to generate a two-dimensional image (still image or video image) indicating said concentration distribution. By using said image information, for example, it is possible to estimate the brain activity (degree of concentration, emotions, or the like) of the subject. The imaging device of the present embodiment can detect biological information such as the aforementioned in a non-contact manner, and can therefore eliminate difficulties associated with detection. In addition, it is possible to eliminate, with a high degree of accuracy, unnecessary signal components produced due to a portion of the signal charge caused by strong surface reflected light that is reflected by the surface of the target object leaking into an accumulation unit. The detection accuracy for biological information can therefore be greatly improved compared to the conventional technology. Hereinafter, a configuration and operation of the imaging device of the present embodiment with which this kind of highly accurate detection is possible will be described.

[1. Configuration]

FIG. 5 is a drawing schematically depicting a configuration of the imaging device 101 in the present embodiment. FIG. 5 depicts not only the imaging device 101 but also the target object 102 (a person's head) that is the detection target. The imaging device 101 of the present embodiment, schematically, has the same configuration as the imaging device 101 in the study example depicted in FIG. 1. However, the present embodiment is different from the aforementioned study example in that there are two light sources and the image sensor 113 has three accumulation units.

The imaging device 101 is provided with the first light source 103, a second light source 104, the image sensor 113, a double bandpass filter 112, an optical system 111, the control circuit 114, and a signal processing circuit 115. The first light source 103 and the second light source 104 emit pulsed light to the front of the imaging device 101 (the direction in which the target object 102 is located). In the present embodiment, the first light source 103 is a laser light source that emits pulsed light of a narrow band having a central wavelength of 750 nm. The second light source 104 is a laser light source that emits pulsed light of a narrow band having a central wavelength of 850 nm. The image sensor 113 is arranged on an image forming surface of the optical system 111 and detects reflected light from the target object 102. The optical system 111 is arranged between the target object 102 and the image sensor 113 and may include one or more lenses. The optical system 111 condenses light from the target object 102 and forms an image on an imaging surface of the image sensor 113. The double bandpass filter 112 is arranged between the optical system 111 and the image sensor 113, and mainly transmits only light having a wavelength of the two narrow bands corresponding to the wavelengths of the light from the first light source 103 and the second light source 104. The control circuit 114 is connected to the first light source 103, the second light source 104, and the image sensor 113, and controls the operations thereof. More specifically, the control circuit 114 synchronously controls the light emission timing of the first light source 103 and the second light source 104, and the timing of the signal accumulation and signal discharge of each pixel of the image sensor 113. It is thereby possible to detect information regarding the cerebral blood flow inside the living body with a high degree of accuracy. The signal processing circuit 115 is connected to the image sensor 113, and generates and outputs image data (for example, two-dimensional video image data) on the basis of light-dark information of each pixel, namely electrical signals that are output from the image sensor 113. The generated image data can be transmitted to a display, which is not depicted, and an image indicating the cerebral blood flow state can be displayed on the display, for example. It should be noted that the signal processing circuit 115 may be provided in a device external to the imaging device 101. For example, the signal processing circuit 115 may be provided in an external computer that is connected to the imaging device 101 in a wired or wireless manner. In this kind of form, the imaging device 101 does not need to perform calculations having a high computational load, and the imaging device 101 can therefore be configured at low cost. It should be noted that the imaging device 101 can include other elements not depicted in FIG. 5. For example, the imaging device 101 may be provided with an optical system such as a mirror that alters the traveling direction of the light from the first light source 103 and the second light source 104, a communication circuit that performs wireless communication, or the like.

It is not necessary for the constituent elements depicted in FIG. 5 to be arranged inside the same casing. For example, the imaging device 101 can be realized by combining an information terminal such as a smartphone or tablet computer, and another device that is connected to the information terminal. This kind of attachment can be provided with the first light source 103, the second light source 104, the image sensor 113, the double bandpass filter 112, and the optical system 111. It is possible to have processors (CPU, GPU, and the like) of an information terminal function as the control circuit 114 and the signal processing circuit 115 by installing specific software in the information terminal.

Hereinafter, the constituent elements will be described in more detail.

[1-1. First Light Source 103 and Second Light Source 104]

The first light source 103 in the present embodiment is a laser pulse light source that emits pulsed light of a narrow band having a central wavelength of 750 nm. The second light source 104 is a laser pulse light source that emits pulsed light of a narrow band having a central wavelength of 850 nm. Each of the first light source 103 and the second light source 104, as described later on, repeatedly emits pulsed light in a predetermined pattern determined by the control circuit 114. The pulsed light emitted by the first light source 103 and the second light source 104 can be light having a square wave shape for which the time from falling starting to falling completing, which is the fall time, is close to zero. The time from rising starting to rising completing, which is the rise time, of pulsed light generated by the first light source 103 and the second light source 104 is arbitrary. The first light source 103 and the second light source 104 can be light sources such as a laser diode (LD) for which the falling portion of the pulsed light is close to vertical with respect to the time axis (in other words, the time response characteristic is rapid). For the first light source 103 and the second light source 104, any type of light source that emits pulsed light such as a semiconductor laser, a solid-state laser, or a fiber laser can be used, for example.

In the imaging device 101 of the present embodiment, since the target object 102 is a person's body, the first light source 103 and the second light source 104 can be used with the effect on the retinas having been taken into consideration. For example, in the case where a laser light source is used, a light source that satisfies class 1 of the laser safety standards drawn up in each country can be used. In the case where class 1 is satisfied, low-illuminance light having an accessible emission limit (AEL) of below 1 mW is radiated onto the target object 102. Even when the first light source 103 and the second light source 104 themselves do not satisfy class 1, by combining with another optical element, class 1 may be satisfied. For example, class 1 of the laser safety standards may be satisfied by having an element such as a diffusion plate or an ND filter arranged between the first and second light sources 103 and 104 and the target object 102 so that the light is diffused or attenuated.

The wavelengths of the light emitted by each of the first light source 103 and the second light source 104 are not restricted to 750 nm and 850 nm. For example, light having any wavelength included in the wavelength range of 650 nm or more and 950 nm or less can be used. The aforementioned wavelength range is referred to as the "biological window", and has the property of it being comparatively difficult for light to be absorbed by water content and hemoglobin inside a living body. In the case where a living body is the detection target, it is possible to improve detection sensitivity by using light having the aforementioned wavelength range. In the case where the concentration of oxygenated hemoglobin and deoxygenated hemoglobin within the cerebral blood flow of the target object 102 is to be detected as in the present embodiment, the light that is used can be near-infrared light having a wavelength longer than 805 nm and red light or near-infrared light having a wavelength shorter than 805 nm. Oxygenated hemoglobin absorbs light having a wavelength longer than 805 nm relatively well compared to deoxygenated hemoglobin. Conversely, deoxygenated hemoglobin absorbs light having a wavelength shorter than 805 nm relatively well compared to oxygenated hemoglobin. Consequently, by using light having a wavelength longer than 805 nm and light having a wavelength shorter than 805 nm, it is possible to detect changes in the concentration of each of oxygenated hemoglobin and deoxygenated hemoglobin in blood flow with good accuracy. In this way, it is possible to analyze characteristics of the detection target by selecting a plurality of wavelengths having different absorption rates with respect to the detection target. In the case where other biological information is to be detected (for example, heart rate, blood flow rate, or blood pressure), it is not necessary to use light having a plurality of wavelengths. As in the configuration depicted in FIG. 1, control similar to that in the present embodiment may be performed by using one first light source 103. Likewise, there may be one light source in the other embodiments described later on.

It should be noted that, in the present disclosure, the target object 102 is not restricted to being living body. For example, it is also possible for other types of light scattering bodies such as gases, medicines, or foods to be set as the target object 102. The wavelength bands of the light emitted by the first light source 103 and the second light source 104 are not restricted to approximately 700 nm or more and approximately 2,500 nm or less, which is the wavelength band of near-infrared rays, and may be approximately 400 nm or more and approximately 700 nm or less, which is the wavelength band of visible light, or approximately 10 nm or more and approximately 400 nm or less, which is the wavelength band of ultraviolet rays, for example. Depending on use, it is also possible to use mid-infrared rays, far-infrared rays, or electromagnetic waves of a radio wave band such as terahertz waves or millimeter waves.

As described with reference to FIG. 1, light that has reached the target object 102 from the first light source 103 and the second light source 104 is divided into the surface reflected component I1, which is the component reflected by the surface of the target object 102, and the internally scattered component I2, which the component that reflects or scatters once or scatters multiple times inside the target object 102. The surface reflected component I1 includes the three components of a directly reflected component, a diffuse-reflected component, and a scatter-reflected component. The directly reflected component is a component that is reflected at a reflection angle that is equal to the incidence angle. The diffuse-reflected component is a component that is diffused and reflected due to irregular shapes of the surface. The scatter-reflected component is a component that is scattered and reflected by internal tissue near the surface. In the case where the target object 102 is a person's skin, the scatter-reflected component is the component that is scattered and reflected inside the skin. In the present disclosure, the surface reflected component 11 includes these three components. Furthermore, the internally scattered component 12 does not include a component that is scattered and reflected by internal tissue near the surface. The traveling directions of the surface reflected component 11 and the internally scattered component 12 change due to reflection or scattering, and a portion thereof passes through the optical system 111 and the double bandpass filter 112 and reaches the image sensor 113.

[1-2. Optical System 111 and Double Bandpass Filter 112]

The optical system 111 in the present embodiment is a camera lens that realizes an telecentric optical system. By using the telecentric optical system 111, it is possible to reduce light that is obliquely incident on the pixels, and it is therefore possible to simplify signal processing as described later on.

Figure 6:
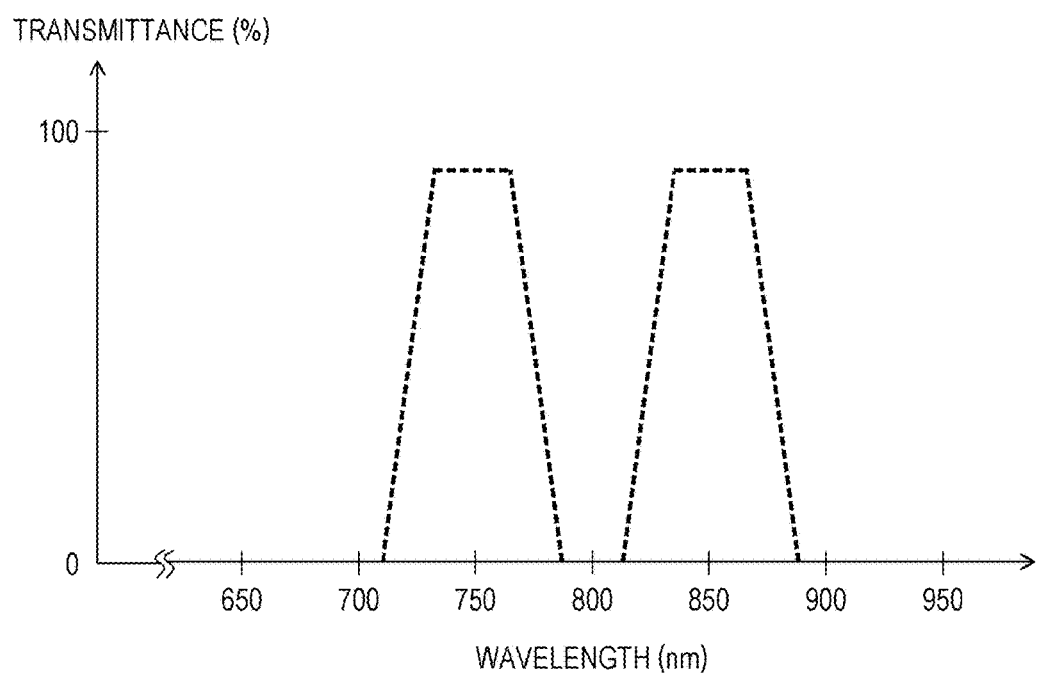
FIG. 6 is a graph depicting an example of the spectral transmittance of a double bandpass filter.

The double bandpass filter 112 is a filter that mainly transmits light having the two wavelengths of 750 nm and 850 nm. FIG. 6 is a graph depicting an example of the spectral transmittance of the double bandpass filter 112. As depicted in the drawing, the double bandpass filter 112 transmits light of the narrow bands having the central wavelengths of 750 nm and 850 nm emitted respectively from the first light source 103 and the second light source 104, and blocks light of other wavelengths. By arranging this kind of double bandpass filter 112, it is possible to suppress the incidence of disturbance light (for example, background light) on the image sensor 113.

[1-3. Image Sensor 113]

The image sensor 113 receives light that is emitted from the first light source 103 and the second light source 104 and reflected by the target object 102. The image sensor 113 has a plurality of pixels arrayed two-dimensionally on the imaging surface, and acquires two-dimensional information regarding inside the target object 102. The image sensor 113 may be a CCD image sensor or a CMOS image sensor, for example.

The image sensor 113 has an electronic shutter. The electronic shutter is a circuit that controls the length (referred to as the "shutter width") of a period for one instance of signal accumulation (referred to as the "exposure period") in which the received light is converted into an effective electrical signal and accumulated, and controls the time from one exposure period finishing to the next exposure period starting. In the present specification, the state in which the electronic shutter allows exposure is expressed as "open" (an open state), and the state in which the electronic shutter stops exposure is expressed as closed (a closed state). The image sensor 113 can adjust the time from one exposure period finishing to the next exposure period starting, on a time scale of sub-nanoseconds (for example, 30 ps to 1 ns) by means of the electronic shutter. In the present embodiment, different from a conventional time-of-flight (TOF) camera that has the purpose of measuring the distance to a target object, it is not necessary for the shutter width to be larger than the pulse width. A conventional TOF camera detects all pulsed light that has been emitted from a light source and has returned having been reflected by a target object, in order to correct the brightness of the target object. Consequently, in a conventional TOF camera, it has been necessary for the shutter width to be larger than the pulse width of light. In contrast, in the imaging device 101 of the present embodiment, it is not necessary for the shutter width to be larger than the pulse width since there is no need to correct the amount of light from the target object. In the present embodiment, the shutter width can be approximately 1 to 30 ns, for example. According to the imaging device 101 of the present embodiment, it is possible to make the shutter width shorter than in the past, and it is therefore possible to reduce dark current included in detection signals.

For uses in which the target object 102 is a person's forehead or the like and information such as the cerebral blood flow is to be detected, the attenuation rate of light inside the target object 102 is extremely high, and light can attenuate to one millionth, for example. Therefore, there are cases where, with only the irradiation of a single pulse, the amount of light may be insufficient to detect the internally scattered light 12. In this case, the first light source 103 and the second light source 104 may emit pulsed light a plurality of times, and accordingly the image sensor 113 may also perform exposure a plurality of times by means of the electronic shutter. According to this kind of operation, it is possible to improve sensitivity by detection signals being integrated.

Figure 7:
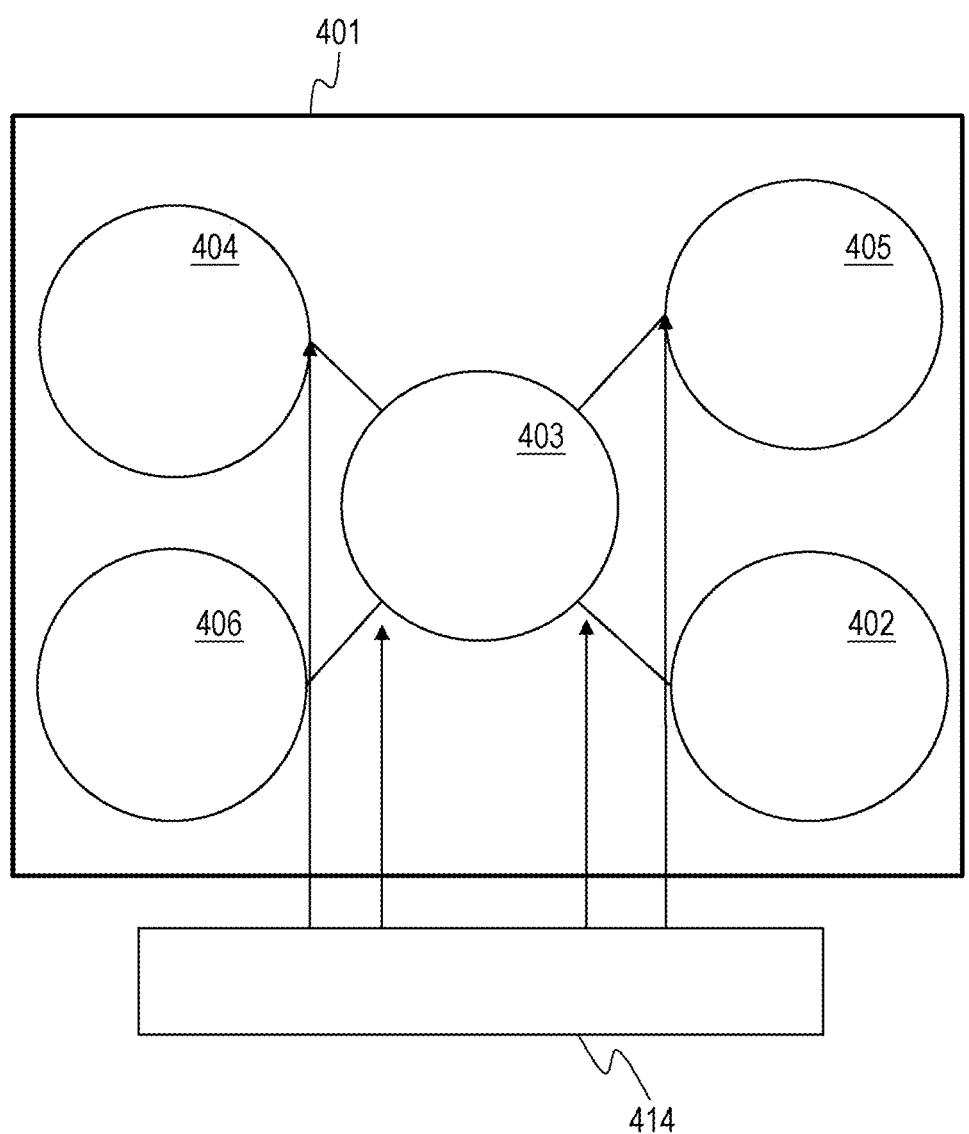
FIG. 7 is a drawing depicting a schematic configuration of one pixel of the image sensor.

FIG. 7 is a drawing depicting a schematic configuration of one pixel 401 of the image sensor image sensor 113. It should be noted that FIG. 7 depicts the configuration of one pixel 401 in a schematic manner, and does not necessarily reflect the actual structure. The pixel 401 includes: the photodiode 403, which is a photoelectric conversion element for performing photoelectric conversion; floating diffusion layers 404, 405, and 406, which are accumulation units for accumulating signal charge; and the drain 402, which is a discharge unit for discharging signal charge. The functions of the floating diffusion layers 404, 405, and 406 and the drain 402 are similar to the functions described with reference to FIG. 2.

The image sensor 113 is provided with the high-speed timing control circuit 414, which controls the accumulation and discharge of signal charge in the pixels 401, on the basis of commands from the control circuit 114. The high-speed timing control circuit 414 can be a circuit that has a processor and a memory (for example, a microcontroller unit). In accordance with a control program stored in the memory, the high-speed timing control circuit 414 controls the accumulation of signal charge in the floating diffusion layers 404, 405, and 406 and the discharge of signal charge to the drain 402 in response to instructions from the external control circuit 114. The image sensor 113 can capture images at a high temporal resolution as a result of having the plurality of floating diffusion layers 404, 405, and 406.

In the present embodiment, the telecentric optical system 111 is arranged at the front surface side of the image sensor 113, and it is therefore feasible for light to leak in an isotropic manner centering on the photodiode 403. Therefore, the floating diffusion layers 404, 405, and 406 may be arranged isotropically or at equal distances with respect to the photodiode 403.

Light that is incident on each of the pixels 401 due to one emission of pulsed light is converted by the photodiode 403 into signal electrons that constitute signal charge. The converted signal electrons are discharged to the drain 402 or allocated to any of the three floating diffusion layers 404, 405, and 406 in accordance with a control signal that is input from the high-speed timing control circuit 414.

Figure 8:
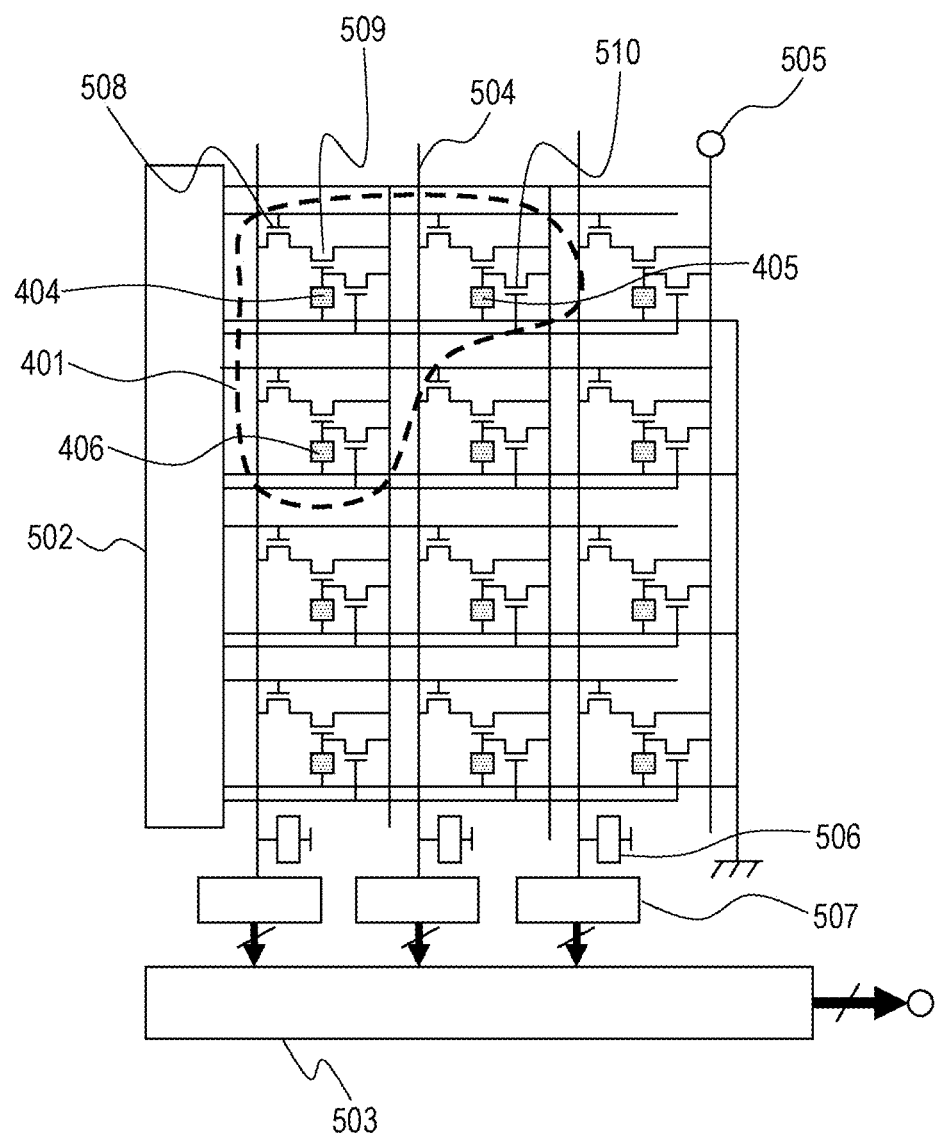
FIG. 8 is a drawing schematically depicting an example of a configuration of the image sensor.

FIG. 8 is a drawing schematically depicting an example of a configuration of the image sensor 113. In FIG. 8, the region surrounded by the dashed line corresponds to one pixel 401. The pixel 401 includes the three floating diffusion layers 404, 405, and 406. Signals accumulated in the three floating diffusion layers 404, 405, and 406 are treated as if they were signals of three pixels of a general CMOS image sensor, and are output from the image sensor 113. It should be noted that FIG. 8 depicts only elements relating to an operation in which the signal charge inside the floating diffusion layers is output from the image sensor 113 once the accumulation of the signal charge has completed in each of the floating diffusion layers (referred to as a "low-speed reading operation"). The drain 402, the photodiode 403, and the high-speed timing control circuit 414 are not directly related to the low-speed reading operation, and have therefore been omitted from FIG. 8.

Each pixel 401 includes three signal detection circuits. Each signal detection circuit includes a source follower transistor 509, a row selection transistor 508, and a reset transistor 510. In this example, the reset transistor 510 corresponds to the drain 402 depicted in FIG. 7. The discharge of signal charge is controlled by a pulse signal that is input to the gate of the reset transistor 510. The transistors are field-effect transistors formed on a semiconductor substrate, for example, but there is no restriction thereto. As depicted in the drawing, one of the input terminal and output terminal of the source follower transistor 509 (typically the source) and one of the input terminal and output terminal of the row selection transistor 508 (typically the drain) are connected. The gate constituting a control terminal of the source follower transistor 509 is electrically connected to the photodiode 403, which is not depicted in FIG. 8. Positive holes or electrons constituting signal charge generated by the photodiode 403 are accumulated in the floating diffusion layers 404, 405, and 406, which are accumulation units between the photodiode 403 and the source follower transistors 509.

The signal charge accumulated in the floating diffusion layers 404, 405, and 406 is read out as a result of the gates of the row selection transistors 508 being set to on by a row selection circuit 502. At such time, current that flows from a source follower power source 505 to the source follower transistors 509 and source follower loads 506 is amplified in accordance with the potential of the signals of the floating diffusion layers 404, 405, and 406. Analog signals produced by this current that are read out from vertical signal lines 504 are converted into digital signal data by analog-digital (AD) conversion circuits 507 that are connected to each column. This digital signal data is read out for each column by a column selection circuit 503, and is output from the image sensor 113. The row selection circuit 502 and the column selection circuit 503 perform reading for one row and then perform reading for the next row, and, likewise thereafter, read out information regarding signal charge of the floating diffusion layers for all rows. After all of the signal charge has been read out, the high-speed timing control circuit 414 resets all of the floating diffusion layers by setting the gates of the reset transistors 510 to on. Imaging for one frame is thereby completed. Likewise, thereafter, imaging for a series of frames by the image sensor 113 is concluded by repeating high-speed imaging for the frames.

In the present embodiment, an example of a CMOS-type image sensor 113 has been described; however, it should be noted that the image sensor 113 may be a CCD type, a single photon counting-type element, or an EMCCD or ICCD, which are amplifying-type image sensors.

[1-4. Control Circuit 114 and Signal Processing Circuit 115]

The control circuit 114 can be an integrated circuit such as a combination of a microprocessor and a memory, or a microcontroller having a processor and a memory housed therein. The control circuit 114 issues lighting instructions for the first light source 103 and the second light source 104, imaging instructions for the image sensor 113, calculation instructions for the signal processing circuit 115, and the like by the processor executing a control program recorded in the memory, for example. The high-speed timing control circuit 414 in the image sensor 113 controls the accumulation and discharge of signal charge in each pixel on the basis of instructions from the control circuit 114.

The signal processing circuit 115 is a circuit that processes image signals that are output from the image sensor 113. The signal processing circuit 115 can be realized by a combination of a digital signal processor (DSP), a programmable logic device (PLD) such as a field-programmable gate array (FPGA), a central processing unit (CPU) or a graphics processing unit (GPU), and a computer program, for example. It should be noted that the control circuit 114 and the signal processing circuit 115 may be realized by means of one integrated circuit.

The signal processing circuit 115 in the present embodiment generates video image data indicating the concentration distribution of oxygenated hemoglobin and deoxygenated hemoglobin within the brain and changes over time therein, on the basis of signals output from the image sensor 113. The signal processing circuit 115 is not restricted to such video image data, and may generate other information. For example, biological information such as the blood flow rate in the brain, blood pressure, blood oxygen saturation level, and heart rate may be generated.

It is known that there is a close relationship between changes in the cerebral blood flow rate or the components in the blood stream (for example, hemoglobin) and the neural activity of a person. For example, the cerebral blood flow rate or the components in the blood change as a result of changes in the activities of nerve cells that occur in accordance with changes in the emotions of a person. Consequently, it is possible to estimate the psychological state of a subject as long as it is possible measure biological information such as changes in the cerebral blood flow rate or the components in the blood. The psychological state of a subject refers to feelings (for example, comfort or discomfort), emotions (for example, feeling at ease, uneasiness, sadness, or anger), health conditions (for example, healthy or fatigued), temperature sensations (for example, hot, cold, or humid), or the like. Furthermore, derived from this, indexes indicating degrees of brain activity such as proficiency, learning level, and concentration are also included in the psychological state. The signal processing circuit 115 may estimate the psychological state of the subject such as the degree of concentration on the basis of changes in the cerebral blood flow rate, and output a signal indicating an estimation result.

[2. Operation]

Next, the operation of the imaging device 101 of the present embodiment will be described.

As described with reference to FIG. 1, the majority of the energy of light having a wavelength of 750 nm or 850 nm radiated onto the head constituting the target object 102 is reflected by the surface of the target object 102. However, a small portion of components reach a deep section of the target object 102 while scattering, and then continue to scatter further. Thus, a very small amount of energy once again reaches the surface of the forehead of the head as an internally scattered component. That portion of light passes through the optical system 111 and the double bandpass filter 112, and reaches the image sensor 113.

The energy of the internally scattered light that reaches the image sensor 113 can attenuate to approximately one ten-thousandth of the energy of the surface reflected light that reaches the image sensor 113. Information regarding brain activity is included in this attenuated light component, and therefore the question of how to eliminate the effect of the surface reflected component constituting high energy noise becomes an important issue.

Thus, the control circuit 114 in the present embodiment, in a manner similar to the example described with reference to FIG. 3, sets the electronic shutter to be closed while the surface reflected component of pulsed light is incident on the pixels of the image sensor 113, and, after the trailing end of the surface reflected component has been incident, switches the electronic shutter to be open while the internally scattered component is incident. Thus, the shutter is maintained in the open state for a period corresponding to a light-emission pulse width, and then the shutter is closed once again. Thereafter, the next pulse is emitted, and the same operation is carried out. By repeating the above operation, it is possible to efficiently eliminate components caused by the surface reflected light, and to detect only components of the internally scattered light that include information on brain activity.

It should be noted that the time from light emission being started to the electronic shutter being switched from closed to open can be determined in advance prior to the start of detection. For example, it is possible to measure the time from light emission being started to the trailing end of the surface reflected component reaching the image sensor 113, by the first light source 103 or the second light source 104 performing preliminary light emission and the image sensor 113 detecting that light, prior to the start of detection. This time may be set as the time from the light emission being started to the electronic shutter being opened.

When the target object 102 is a person's forehead and information such as the cerebral blood flow is to be detected, the attenuation rate of internal light is extremely high, and therefore the amount of light with only the irradiation of a single pulse may be insufficient to detect only the internally scattered light. Therefore, in the present embodiment, pulsed light is emitted a plurality of times, and exposure is accordingly performed a plurality of times by the electronic shutter of the image sensor 113. Therefore, detection signals are integrated, and it is thereby possible to improve sensitivity. However, depending on use, there may also be cases where light emission and exposure do not have to be carried out a plurality of times. In such cases, light emission and exposure are carried out once in one frame period for each light source.

As previously mentioned, not all of the signal charge is discharged even if the electronic shutter is closed. A portion of the signal charge caused by strong surface reflected light leaks into each of the floating diffusion layers. Thus, in the present embodiment, the floating diffusion layer 406, which is set to be constantly inactive, is arranged in order to detect the amount of this leaked signal charge. In the present embodiment, the floating diffusion layers 404 and 405 correspond to a first accumulation unit in the present disclosure, and the floating diffusion layer 406 corresponds to a second accumulation unit in the present disclosure.

Figure 9:
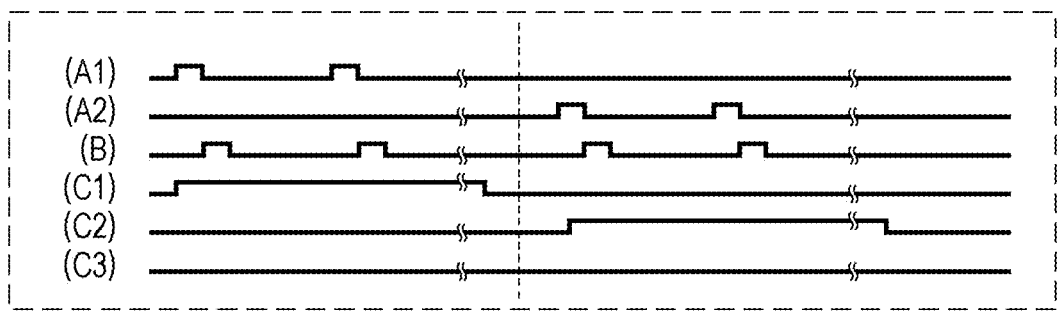
FIG. 9 is a timing chart depicting an example of an operation of the imaging device in embodiment 1.

FIG. 9 is a timing chart depicting an example of an operation of the imaging device 101 in the present embodiment. In FIG. 9, signals A1 and A2 respectively indicate waveforms of pulsed light emitted from the first light source 103 and the second light source 104, signal B indicates the opening and closing timings of the electronic shutter, and signals C1, C2, and C3 respectively indicate the on timings (in other words, the state in which charge is accumulated in the floating diffusion layers) and the off timings (in other words, the state in which charge is not accumulated in the floating diffusion layers) of the floating diffusion layers 404, 405, and 406.

FIG. 9 exemplifies an operation in a period (referred to as a "frame period") in which an image signal of one frame is acquired. One frame period is divided into a period in which imaging is performed using the first light source 103 that emits light having a wavelength of 750 nm, and a period in which imaging is performed using the second light source 104 that emits light having a wavelength of 850 nm. The control circuit 114 first causes the first light source 103 to emit light a plurality of times at a predetermined cycle, and causes signal charge to be accumulated in the floating diffusion layer 404 in synchronization with said emission of light. Next, the control circuit 114 causes the second light source 104 to emit light a plurality of times at a predetermined cycle, and causes signal charge to be accumulated in the floating diffusion layer 405 in synchronization with said emission of light. The signal charge accumulated in the floating diffusion layer 404 is used to generate an image that is based on light having a wavelength of 750 nm. The signal charge accumulated in the floating diffusion layer 405 is used to generate an image that is based on light having a wavelength of 850 nm. Hereinafter, this operation will be described in detail.

The control circuit 114 first causes the first light source 103, which emits light having a wavelength of 750 nm, to emit pulsed light a plurality of times. For example, the control circuit 114 causes the first light source 103 to repeatedly emit pulsed light having a pulse width of approximately 10 ns, approximately 1,000 times over a period of approximately 100 μsec at a frequency of approximately 10 MHz. While the first light source 103 repeatedly emits light, the floating diffusion layer 404 is set to be in an active state, and the floating diffusion layers 405 and 406 are set to be in an inactive state. In this state, the electronic shutter is switched between open and closed states in synchronization with the emission of light by the first light source 103. More specifically, the high-speed timing control circuit 414 in the image sensor 113, as described with reference to FIG. 1, sets the potential of the drain 402 to be relatively high for the electronic shutter to be open, during periods in which the internally scattered component of pulsed light from the target object 102 is incident on the photodiode 403. In periods other than said period, the high-speed timing control circuit 414 sets the potential of the drain 402 to be relatively low for the electronic shutter to be closed. By means of such control, signal charge generated by the photodiode 403 caused by the internally scattered light from the target object 102 is repeatedly accumulated in the floating diffusion layer 404.

When the accumulation of signal charge in the floating diffusion layer 404 has completed, the control circuit 114 sets the floating diffusion layer 404 to inactive and, instead, sets the floating diffusion layer 405 to active. The floating diffusion layer 406 remains inactive. In this state, the control circuit 114 causes the second light source 104 that emits light having a wavelength of 850 nm to start emitting pulsed light. The emission of pulsed light by the second light source 104 can also be carried out at the same frequency, pulse width, and number of times as the emission of pulsed light by the first light source 103. Hereinafter, the electronic shutter is switched between open and closed states in synchronization with the emission of light by the second light source 104. The high-speed timing control circuit 414 sets the potential of the drain 402 to be relatively high for the electronic shutter to be open, during periods in which the internally scattered component of the pulsed light from the target object 102 is incident on the photodiode 403. In periods other than said period, the high-speed timing control circuit 414 sets the potential of the drain 402 to be relatively low for the electronic shutter to be closed. By means of such control, the signal charge generated by the photodiode 403 caused by the internally scattered light from the target object 102 is repeatedly accumulated in the floating diffusion layer 405.

When the above operation has completed, the control circuit 114 causes the image sensor 113 to generate electrical signals that are based on the signal charge accumulated in each of the floating diffusion layers 404, 405, and 406. The image sensor 113 sends the generated electrical signals to the signal processing circuit 115. The signal processing circuit 115 generates a pixel signal corresponding to the wavelength of the light from the first light source 103, by subtracting the signal that is based on the signal charge accumulated in the floating diffusion layer 406 from the signal that is based on the signal charge accumulated in the floating diffusion layer 404. Likewise, a pixel signal corresponding to the wavelength of the light from the second light source 104 is generated by subtracting the signal that is based on the signal charge accumulated in the floating diffusion layer 406 from the signal that is based on the signal charge accumulated in the floating diffusion layer 405. By performing this kind of calculation for each pixel, it is possible to obtain a signal for each pixel of an image that corresponds to each of the wavelengths of 750 nm and 850 nm. According to the above processing, the signal processing circuit 115 generates image data for each of the wavelengths of 750 nm and 850 nm.

[3. Effects Etc.]

As mentioned above, the imaging device in the present embodiment is provided with: the first light source 103 and the second light source 104 which emit pulsed light that is radiated onto the target object; the image sensor 113; the control circuit 114; and the signal processing circuit 115. The image sensor 113 has a plurality of pixels, and each pixel has a photoelectric conversion element and three accumulation units that accumulate signal charge generated by the photoelectric conversion element. The first light source 103 emits pulsed light of a first wavelength band (for example, a wavelength band centering on 750 nm). The second light source 104 emits pulsed light of a second wavelength band (for example, a wavelength band centering on 850 nm). The control circuit 114 controls the timing at which the first light source 103 is made to emit pulsed light, the timing at which the three accumulation units are made to accumulate signal charge, and the timing at which signal charge is discharged. The control circuit 114 executes the following operations.

(1) In one frame period, each of the first light source 103 and the second light source 104 is made to emit pulsed light. (2) In a period that includes at least a period in which, from within the pulsed light emitted from each of the first light source 103 and the second light source 104, the surface reflected component 11 reflected by the surface of the target object 102 is incident on the image sensor 113, a state is implemented in which signal charge is discharged to the drain 402, and the floating diffusion layer 406 is made to accumulate the signal charge that has remained without being discharged, from within the signal charge generated by the photodiode 403. (3) In a period in which, from within the pulsed light having a central wavelength of 750 nm emitted from the first light source 103, the internally scattered component l2 that has scattered inside the target object and returned after the trailing end of the surface reflected component l1 has been incident on the image sensor 113 is incident on the image sensor 113, a state is implemented in which the signal charge is accumulated in the floating diffusion layer 404 without being discharged to the drain 402, and the floating diffusion layer 404 is made to accumulate the signal charge. (4) In a period in which, from within the pulsed light having a central wavelength of 850 nm emitted from the second light source 104, the internally scattered component l2 that has scattered inside the target object and returned after the trailing end of the surface reflected component l1 has been incident on the image sensor 113 is incident on the image sensor 113, a state is implemented in which the signal charge is not discharged to the drain 402, and the floating diffusion layer 404 is made to accumulate the signal charge. (5) After the accumulation of the signal charge to the floating diffusion layers 404, 405, and 406 has completed, the image sensor 113 is made to generate a signal S1 that is based on the signal charge accumulated in the floating diffusion layer 404, a signal S2 that is based on the signal charge accumulated in the floating diffusion layer 405, and a signal S3 that is based on the signal charge accumulated in the floating diffusion layer 406.

The signal processing circuit 115 generates a signal for each pixel of an image produced by the light having a central wavelength of 750 nm by subtracting the signal S3 from the signal S1 for each pixel. Likewise, a signal for each pixel of an image produced by the light having a wavelength of 850 nm is generated by subtracting the signal S3 from the signal S2 for each pixel.

According to the above configuration and operation, a noise component included in each of the signals of the floating diffusion layers 404 and 405 can be detected by the floating diffusion layer 406 and eliminated. It is thereby possible to obtain a signal that is based on the light scattered inside the living body, with a high degree of accuracy.

In the present embodiment, the two light sources of the first light source 103 and the second light source 104 are used; however, only one light source may be used. In the case where only one light source is used, only operations to perform light exposure or signal accumulation from among the operations depicted in FIG. 9 may be carried out using either one of the light sources. The same is also true for other embodiments described later on.

Embodiment 2

Next, the imaging device 101 in embodiment 2 of the present disclosure will be described. The present embodiment is different from embodiment 1 in that the optical system 111 is a non-telecentric optical system, and in that imaging in a state in which none of the floating diffusion layers are active is carried out as calibration prior to detection. Hereinafter, a description will be given focusing on the differences with embodiment 1.

Figure 10:
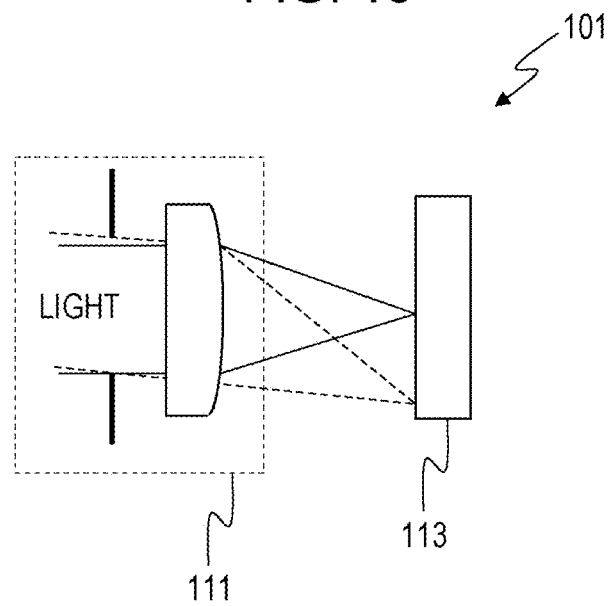
FIG. 10 is a drawing schematically depicting an image sensor and an optical system in an imaging device of embodiment 2.

FIG. 10 is a drawing schematically depicting the image sensor 113 and the optical system 111 in the imaging device 101 of the present embodiment. The optical system 111 in the present embodiment is a lens system in which the chief ray is obliquely incident on a peripheral section of the image sensor 113 (in other words, the chief ray angle is greater than 0 degrees). In embodiment 1, a comparatively expensive telecentric optical system is used as a camera lens; however, non-telecentric optical systems that are inexpensive lens systems are generally often used. In the case where a non-telecentric optical system 111 is used, the chief ray angle is different between the center section and peripheral section of the imaging surface of the image sensor 113. Therefore, in each floating diffusion layer, a deviation occurs in the amount of the leakage component caused by light reflected by the living body surface.

In the present embodiment, in the first frame period, a calibration frame is provided in which a transfer to any of the floating diffusion layers is also obtained in an inactive (off) state. In the second frame period and thereafter, similar to embodiment 1, a transfer to a specific floating diffusion layer is obtained in an active (on) state. By providing the calibration frame, it is possible to acquire information on the distribution of the components of light that leak into each of the floating diffusion layers. By using this distribution information, it is possible to accurately eliminate leakage components from acquired signals even when there is a deviation in the amount of signal charge that leaks into each of the floating diffusion layers.

Figure 11A:
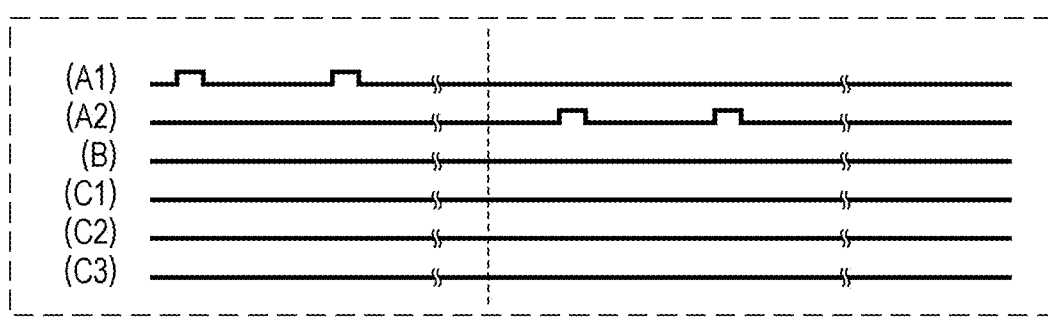
FIG. 11A is a timing chart depicting an operation for acquiring a signal in a first frame period in embodiment 2.
Figure 11B:
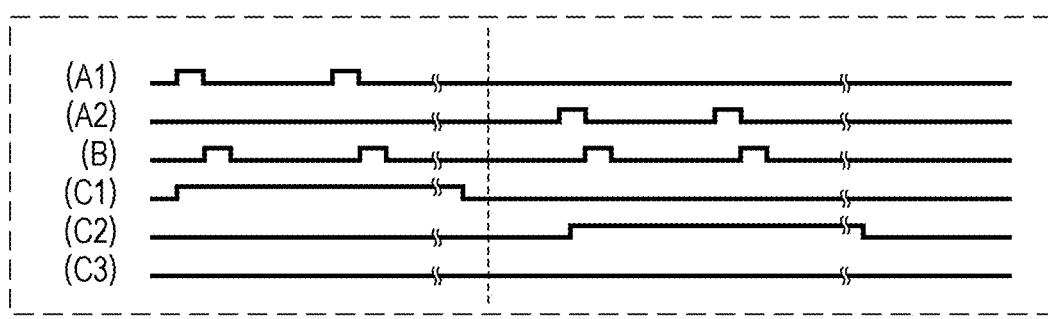
FIG. 11B is a timing chart depicting an operation for acquiring a signal in a second frame period in embodiment 2.

FIG. 11A is a timing chart depicting an operation for acquiring a signal in the first frame period in the present embodiment. FIG. 11B is a timing chart depicting an operation for acquiring a signal in the second frame period in the present embodiment.

In the first frame period, the control circuit 114 depicted in FIG. 7 first causes the first light source 103, which emits light having a wavelength of 750 nm, to emit pulsed light a plurality of times. For example, the control circuit 114 causes the first light source 103 to repeatedly emit pulsed light having a pulse width of approximately 10 ns, approximately 1,000 times over a period of approximately 100 µsec at a frequency of approximately 10 MHz. While light emission by the first light source 103 is being repeated, the floating diffusion layers 404, 405, and 406 are constantly set in an inactive state, and the electronic shutter is constantly set in a closed state. Thereafter, the control circuit 114 performs the same operation also for the second light source 104 that emits light having a wavelength of 850 nm. While light emission by the second light source 104 is being repeated, the floating diffusion layers 404, 405, and 406 are constantly set in an inactive state, and the electronic shutter is constantly set in a closed state. Due to this operation, in each of the floating diffusion layers 404, 405, and 406, signal charge caused by the light that has scattered inside the living body is not accumulated, and only a leaking noise component caused by the light that has been reflected by the surface of the living body is accumulated.

In the second frame period and thereafter, as depicted in FIG. 11B, operations that are the same as the operations (FIG. 9) in embodiment 1 are carried out. In other words, the control circuit 114 repeats, in an alternating manner, an operation to cause the floating diffusion layer 404 to accumulate signal charge while causing the first light source 103 to periodically emit light, and an operation to cause the floating diffusion layer 405 to accumulate signal charge while causing the second light source 104 to periodically emit light. The floating diffusion layer 406 is constantly inactive. Thus, signal charge caused by the internally scattered component of pulsed light having a central wavelength of 750 nm emitted by the first light source 103 is accumulated in the floating diffusion layer 404. Signal charge caused by the internally scattered component of pulsed light having a central wavelength of 850 nm emitted by the second light source 104 is accumulated in the floating diffusion layer 405. From within the signal charge caused by the surface reflected component of the light emitted by the first light source 103 and the second light source 104, the leakage component, which is signal charge that has not been discharged to the drain 402, is accumulated in the floating diffusion layer 406.

In the present embodiment, the optical system 111 is an inexpensive non-telecentric optical system, and therefore there is a difference in the amount of the leakage component included in the signal charge accumulated in the floating diffusion layer 404 and the amount of the leakage component included in the signal charge accumulated in the floating diffusion layer 405. In addition, the ratio between both amounts is different depending on the pixel. Thus, in the present embodiment, the signal processing circuit 115 corrects the signals of the floating diffusion layers 404 and 405 that are acquired in the second frame period and thereafter, using the signals of the floating diffusion layers 404, 405, and 406 that are acquired during the first frame period.

Hereinafter, a method for calculating the component of light scattered by the living body in the present embodiment is described with reference to FIG. 12.

FIG. 12 is a drawing schematically depicting frame periods and signal amounts of each of the floating diffusion layers 404, 405, and 406 in the present embodiment. In FIG. 12, an example of four consecutive frame periods is given.

In the first frame period, all of the floating diffusion layers 404, 405, and 406 are in an off state, and therefore leakage components of a 750-nm optical signal and an 850-nm optical signal are accumulated in each of the floating diffusion layers 404, 405, and 406. In imaging during the first frame period, the signal amounts accumulated in the floating diffusion layers 404, 405, and 406 are respectively expressed as $C_{1\_FD1}$, $C_{1\_FD2}$, and $C_{1\_FD3}$. Furthermore, in imaging during an $n^{th}$ frame period (n being an integer of 2 or more), the signal amounts accumulated in the floating diffusion layers 404, 405, and 406 are respectively expressed as $a_n$, $b_n$, and $C_{n\_FD3}$. $a_n$ includes a signal amount caused by internally scattered light having a wavelength of 750 nm, and a signal amount caused by leakage components of the 750-nm optical signal and the 850-nm optical signal. $b_n$ includes a signal amount caused by internally scattered light having a wavelength of 850 nm, and a signal amount caused by leakage components of the 750-nm optical signal and the 850-nm optical signal. $C_{n\_FD3}$ includes a signal amount caused by leakage components of the 750-nm optical signal and the 850-nm optical signal.

The signal processing circuit 115 in the present embodiment eliminates leakage components from signal components of the floating diffusion layers 404 and 405 by carrying out the following calculation.

The signal component having a wavelength of 750 nm and the signal component having a wavelength of 850 nm in the second frame period are obtained by means of the following calculation using a signal amount $a_2$ of the floating diffusion layer 404, a signal amount $b_2$ of the floating diffusion layer 405, a signal amount $C_{2\_FD3}$ of the floating diffusion layer 406, and signal amounts $C_{1\_FD1}$, $C_{1\_FD2}$, and $C_{1\_FD3}$ of each of the floating diffusion layers 404, 405, and 406 detected in the first frame period.

$$\text{750-nm wavelength signal component} = a_2 - C_{2\_FD3} \times C_{1\_FD1}/C_{1\_FD3}$$

$$\text{850-nm wavelength signal component} = b_2 - C_{2\_FD3} \times C_{1\_FD2}/C_{1\_FD3}$$

Likewise, for the $n^{th}$ frame period of the third frame period and thereafter, the 750-nm wavelength signal component and the 850-nm wavelength signal component are obtained by means of the following calculation.

750-nm wavelength signal component=$a_n - C_{n\_FD3} \times C_{1\_FD1}/C_{1\_FD3}$ 850-nm wavelength signal component=$b_n - C_{n\_FD3} \times C_{1\_FD2}/C_{1\_FD3}$ In the present embodiment, all of the floating diffusion layers 404, 405, and 406 are set to an off state in the first frame period; however, all of the floating diffusion layers 404, 405, and 406 may be set to off in any frame period. For example, taking into consideration that the leakage component amount fluctuates due to the influence of the accumulation of heat in the image sensor 113 and the like, a leakage component may be detected with all of the floating diffusion layers 404, 405, and 406 being set to off in a specific frame period cycle.

As mentioned above, in the present embodiment, in another frame period (for example, the first frame period) that is different from a normal frame period, in a period that includes at least a period in which the surface reflected component of pulsed light is incident on the image sensor, the control circuit 114 implements a state in which signal charge is discharged to the drain 402, and causes the floating diffusion layers 404, 405, and 406 to accumulate signal charge that has remained without being discharged, from within the signal charge generated by the photoelectric conversion element. Then, after the accumulation of signal charge to the floating diffusion layers 404, 405, and 406 has completed, the control circuit 114 causes the image sensor 113 to generate signals that are based on the signal charge accumulated in each of the floating diffusion layers 404, 405, and 406. Here, the signals of the floating diffusion layers 404, 405, and 406 in a normal frame period (FIG. 11B) are respectively S1, S1', and S2, and the signals of the floating diffusion layers 404, 405, and 406 in the calibration frame (FIG. 11A) are respectively S3, S3', and S4. The signal processing circuit 115 generates a signal S obtained by means of the calculation S=S1−S2×S3/S4, as a pixel signal in a frame having a central wavelength of 750 nm. Likewise, the signal processing circuit 115 generates a signal S' obtained by means of the calculation S'=−S2×S3'/S4, as a pixel signal in a frame having a central wavelength of 850 nm.

According to this kind of operation, leakage components can be correctly eliminated from the signal components accumulated in the floating diffusion layers 404, 405, and 406, even in the case where a deviation occurs in the distribution of the leakage components in the floating diffusion layers 404, 405, and 406. According to the present embodiment, it is possible to use a comparatively inexpensive non-telecentric optical system 111. Furthermore, it is not necessary for the floating diffusion layers 404, 405, and 406 to be arranged isotropically from the photodiode. Therefore, the degree of freedom in the design for the imaging device 101 can be increased.

Embodiment 3

Next, the imaging device 101 in embodiment 3 of the present disclosure will be described. The imaging device 101 of the present embodiment is different from embodiment 2 in that the combination of the two floating diffusion layers for detecting the internally scattered component and the floating diffusion layer for detecting the leakage component is changed in each frame period. According to the present embodiment, it is possible to generate a biological signal from which the leakage component has been eliminated, without using a calibration frame. Hereinafter, a description will be given focusing on the difference with embodiment 2.

The imaging device 101 in the present embodiment, similar to embodiments 1 and 2, has the configuration depicted in FIG. 5. In the present embodiment, the non-telecentric optical system 111 is used. In the present embodiment, the signal processing circuit 115 has the function of detecting motion of the target object 102, and, as required, updating a coefficient that is used for signal correction, at a timing when the target object 102 is not moving. The signal processing circuit 115 can detect motion at each point in an image on the basis of changes over time in luminance information of each pixel that is output from the image sensor 113.

Figure 13A:
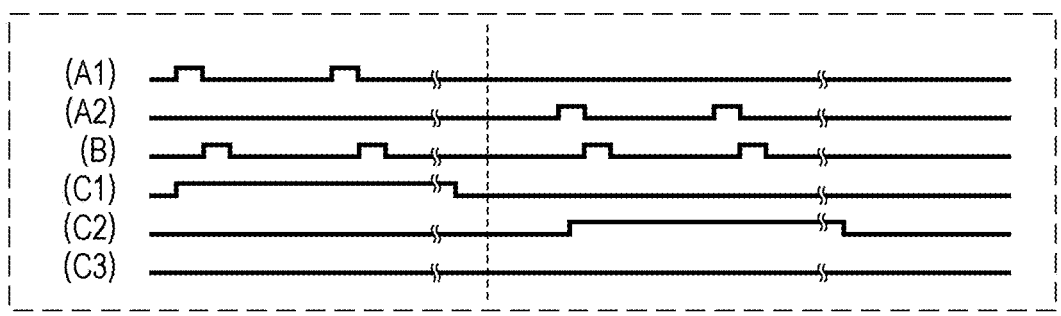
FIG. 13A depicts system timings in a first frame period in embodiment 3.
Figure 13B:
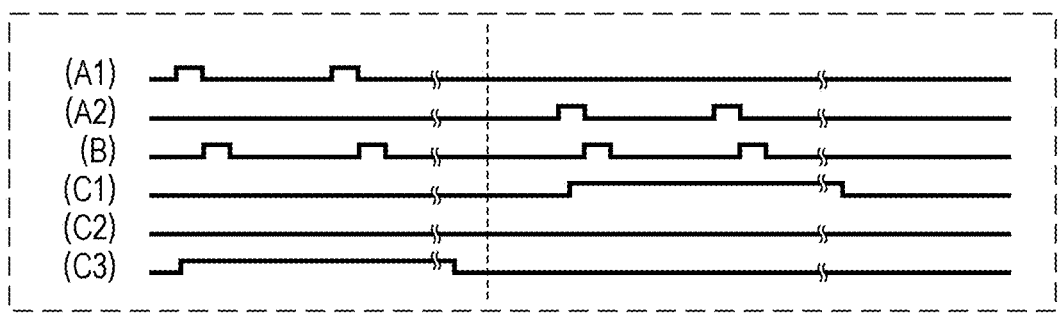
FIG. 13B depicts system timings in a second frame period in embodiment 3.
Figure 13C:
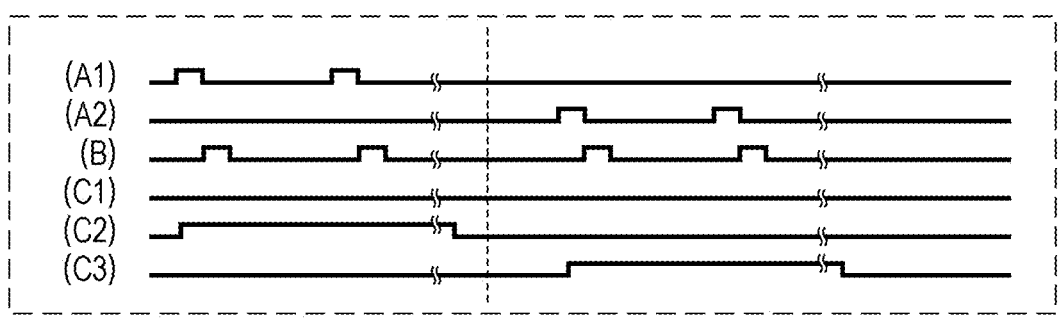
FIG. 13C depicts system timings in a third frame period in embodiment 3.

FIGS. 13A to 13C are timing charts depicting a control method in the present embodiment. FIG. 13A depicts system timings in a first frame period. FIG. 13B depicts system timings in a second frame period. FIG. 13C depicts system timings in a third frame period. The operations depicted in FIGS. 13A to 13C are sequentially repeated in the fourth frame period and thereafter.

The operation in the first frame period depicted in FIG. 13A is the same as the operation (FIG. 9) in embodiment 1 and the operation (FIG. 11B) carried out when a signal in a normal frame period is to be acquired in embodiment 2. In other words, the control circuit 114 sequentially carries out an operation to cause the floating diffusion layer 404 to accumulate signal charge while causing the first light source 103 to periodically emit light, and an operation to cause the floating diffusion layer 405 to accumulate signal charge while causing the second light source 104 to periodically emit light. The floating diffusion layer 406 is constantly inactive. Thus, signal charge caused by the internally scattered component of pulsed light having a central wavelength of 750 nm emitted by the first light source 103 is accumulated in the floating diffusion layer 404. Signal charge caused by the internally scattered component of pulsed light having a central wavelength of 850 nm emitted by the second light source 104 is accumulated in the floating diffusion layer 405. From within the signal charge caused by the surface reflected component of the light emitted by the first light source 103 and the second light source 104, the leakage component, which is signal charge that has not been discharged to the drain 402, is accumulated in the floating diffusion layer 406.

The operation in the second frame period depicted in FIG. 13B corresponds to an operation in which the roles of the floating diffusion layers 404, 405, and 406 in the first frame period have been switched. The operations of the first light source 103, the second light source 104, and the electronic shutter are the same as in the first frame period. In the second frame period, in a period during which the first light source 103 emits light, the floating diffusion layer 406 is set to be active and the floating diffusion layers 404 and 405 are set to be inactive. On the other hand, in a period during which the second light source 104 emits light, the floating diffusion layer 404 is set to be active and the floating diffusion layers 405 and 406 are set to be inactive. Thus, signal charge caused by the internally scattered component of pulsed light having a central wavelength of 750 nm emitted by the first light source 103 is accumulated in the floating diffusion layer 406. Signal charge caused by the internally scattered component of pulsed light having a central wavelength of 850 nm emitted by the second light source 104 is accumulated in the floating diffusion layer 404. From within the signal charge caused by the surface reflected component of the light emitted by the first light source 103 and the second light source 104, the leakage component, which is signal charge that has not been discharged to the drain 402, is accumulated in the floating diffusion layer 405.

The operation in the third frame period depicted in FIG. 13C corresponds to an operation in which the roles of the floating diffusion layers 404, 405, and 406 in the second frame period have been further switched. The operations of the first light source 103, the second light source 104, and the electronic shutter are the same as in the first frame and the second frame. In the third frame, in a period during which the first light source 103 emits light, the floating diffusion layer 405 is set to be active and the floating diffusion layers 404 and 406 are set to be inactive. On the other hand, in a period during which the second light source 104 emits light, the floating diffusion layer 406 is set to be active and the floating diffusion layers 404 and 405 are set to be inactive. Thus, signal charge caused by the internally scattered component of pulsed light having a central wavelength of 750 nm emitted by the first light source 103 is accumulated in the floating diffusion layer 405. Signal charge caused by the internally scattered component of pulsed light having a central wavelength of 850 nm emitted by the second light source 104 is accumulated in the floating diffusion layer 406. From within the signal charge caused by the surface reflected component of the light emitted by the first light source 103 and the second light source 104, the leakage component, which is signal charge that has not been discharged to the drain 402, is accumulated in the floating diffusion layer 404.

The operations depicted in FIGS. 13A to 13C are sequentially repeated in the fourth frame period and thereafter. In this way, in the present embodiment, the floating diffusion layer that accumulates signal charge caused by 750-nm internally scattered light, the floating diffusion layer that accumulates signal charge caused by 850-nm internally scattered light, and the floating diffusion layer that accumulates the leakage component of signal charge are rotated in each frame period. According to this kind of operation, it is possible to eliminate unnecessary components from signals without providing the calibration frame provided in embodiment 2.

Hereinafter, the signal processing in the present embodiment will be described with reference to FIGS. 14 and 15.

Figure 14:
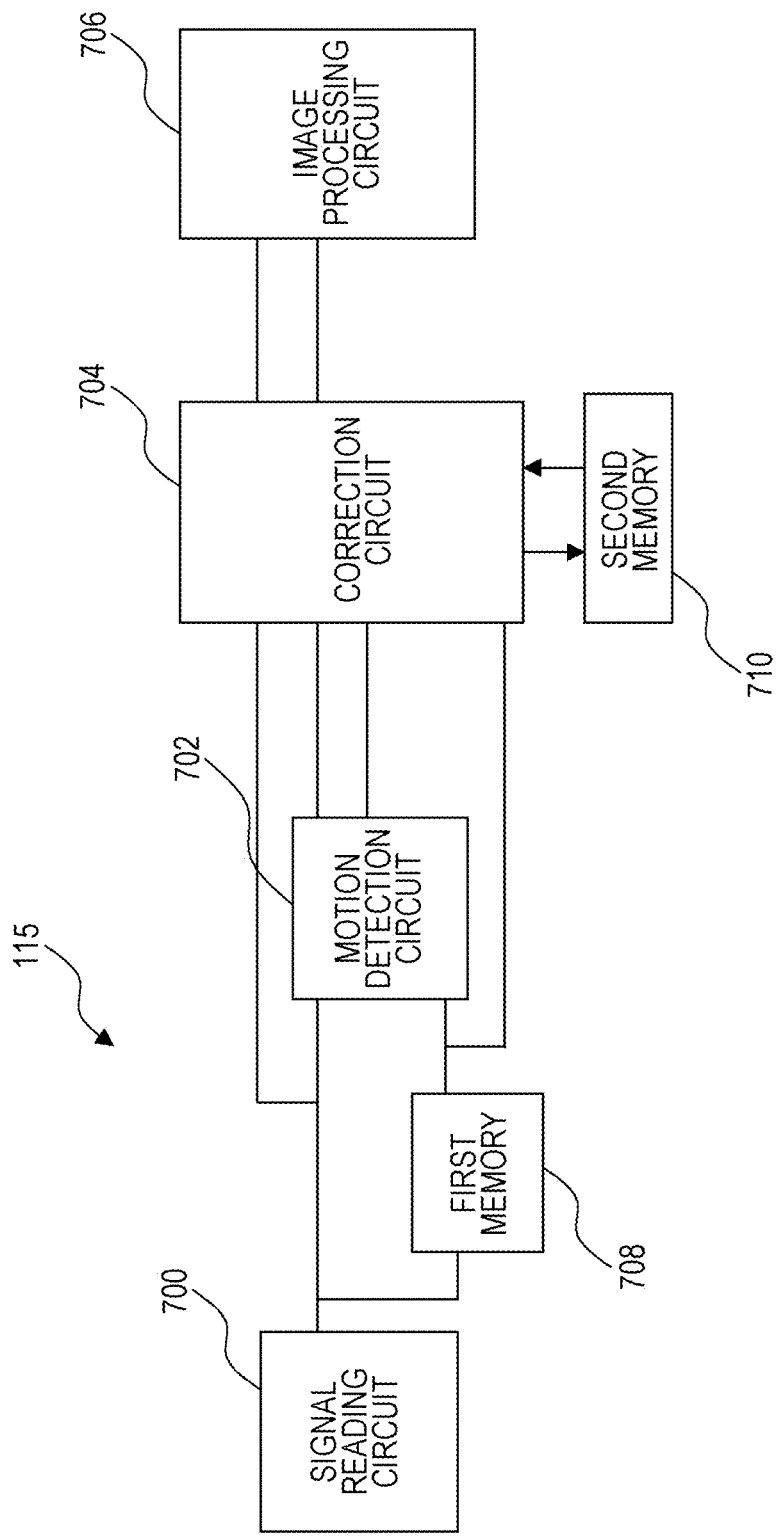
FIG. 14 is a block diagram schematically depicting a configuration of a signal processing circuit in embodiment 3.

FIG. 14 is a block diagram schematically depicting a configuration of the signal processing circuit 115 in the present embodiment. As depicted in the drawing, the signal processing circuit 115 includes: a signal reading circuit 700 that executes processing for reading a signal from the image sensor 113; a motion detection circuit 702 that executes processing for detecting motion of the target object 102; a correction circuit 704 that executes processing for correcting a signal; and an image processing circuit 706 that executes processing for generating data of an image on the basis of the corrected signal. These items of processing can be executed by a processor in the signal processing circuit 115 executing a program stored in a memory, for example. The signal processing circuit 115 includes: a first memory 708 that is a frame memory for recording a signal of each frame period that is output from the image sensor 113; and a second memory 710 that records a coefficient used for correction processing. The first memory 708 and the second memory 710 may be memories that are the same or may be different memories.

FIG. 15 is a drawing for describing a specific example of signal processing in the present embodiment. FIG. 15 depicts examples of the signal amounts of the floating diffusion layers 404, 405, and 406 in one pixel in an $n^{th}$ frame period (n being an integer of 2 or more) to an $n+7^{th}$ frame period, whether or not the target object 102 has moved, and the signal amounts of the floating diffusion layers 404, 405, and 406 after correction.

In FIG. 15, the floating diffusion layers 404, 405, and 406 are respectively expressed as FD1, FD2, and FD3. In FIG. 15, a signal amount obtained by a leakage component being superimposed on a component of internally scattered light having a wavelength of 750 nm is expressed as a, a signal amount obtained by a leakage component being superimposed on a component of internally scattered light having a wavelength of 850 nm is expressed as b, and a signal amount indicating a leakage component is expressed as c. The subscript portion corresponds to the number of the frame period, where the number obtained by subtracting n from the sequential order of the frame period and adding 1 is taken as the number of that frame period; for example, the number of the $n^{th}$ frame period is "1" and the number of the $n+1^{th}$ frame period is "2". As depicted in FIG. 15, for example, in signal reading processing, in a $n^{th}$ frame period, the signal amount of the floating diffusion layer 404 is $a_1$, the signal amount of the floating diffusion layer 405 is $b_1$, and the signal amount of the floating diffusion layer 406 is $c_1$. In the $n+1^{th}$ frame period, the signal amount of the floating diffusion layer 404 is $b_2$, the signal amount of the floating diffusion layer 405 is $c_2$, and the signal amount of the floating diffusion layer 406 is $a_2$. In the $n+2^{th}$ frame period, the signal amount of the floating diffusion layer 404 is $c_3$, the signal amount of the floating diffusion layer 405 is $a_3$, and the signal amount of the floating diffusion layer 406 is $b_3$. Likewise, in the frame periods thereafter, each signal amount is expressed by means of the characters indicated in FIG. 15. "Frame memory reading" in FIG. 15 refers to processing for reading the signal amounts of the floating diffusion layers 404, 405, and 406 of the same pixel in the immediately preceding frame period, recorded in the frame memory.

In the present embodiment, a corrected signal is obtained by subtracting an amount obtained by multiplying the signal amount expressed by the character c by a correction coefficient, from the signal amount expressed by the characters a and b. Here, coefficients α and β are defined as follows.

$$\alpha = C_{\_FD2}/C_{\_FD1}$$

$$\beta = C_{\_FD3}/C_{\_FD1}$$

$C_{\_FD1}$, $C_{\_FD2}$, and $C_{\_FD3}$ respectively express signal amounts of leakage components that have already been detected using the floating diffusion layers 404, 405, and 406. However, $C_{\_FD1}$ and $C_{\_FD2}$ used to determine α are values that are obtained in two frame periods in which the target object 102 has not moved. Likewise, $C_{\_FD1}$ and $C_{\_FD3}$ used to determine β are values that are obtained in another two frame periods in which the target object 102 has not moved.

In the example depicted in FIG. 15, value $\alpha_1$ is already determined as coefficient α and value $\beta_1$ is already determined as coefficient β prior to detection for the $n^{th}$ frame period. A signal amount indicating an internally scattered component is corrected using these coefficients $\alpha_1$ and $\beta_1$.

In the $n^{th}$ frame period, the 750-nm wavelength signal component, the 850-nm wavelength signal component, and the leakage component are expressed by means of the following formulas, for example.

$$\text{750-nm wavelength signal component} = a_1 - c_1 \times c_{\_FD1}/c_{\_FD3} = a_1 - c_1/\beta_1$$

850-nm wavelength signal component=$b_1 - c_1 \times$
$c\_{FD2}/c\_{FD3} = b_1 - c_1/\beta_1 \times \alpha_1$ Leakage component=$c_1$ $\alpha_1$ and $\beta_1$ are determined prior to detection for the $n^{th}$ frame period and are written to the second memory. $\alpha_1$ is the ratio between the leakage component detected by the floating diffusion layer 405 and the leakage component detected by the floating diffusion layer 404 in two consecutive frame periods in which the target object 102 has not moved. $\beta_1$ is the ratio between the leakage component detected by the floating diffusion layer 406 and the leakage component detected by the floating diffusion layer 404 in two consecutive frame periods in which the target object 102 has not moved. The signal processing circuit 115 acquires the signals $a_1$, $b_1$, and $c_1$ from the image sensor 113, acquires the coefficients $\alpha_1$ and $\beta_1$ from the second memory, and performs the calculation of the above formula to thereby correct the signals of the floating diffusion layer 404 and the floating diffusion layer 405.

In the $n+1^{th}$ frame period, the 750-nm wavelength signal component, the 850-nm wavelength signal component, and the leakage component are expressed by means of the following formulas.

750-nm wavelength signal component=$a_2 c_2 \times c\_{FD3}/$
$c\_{FD2} = a_2 - c_2 \times \beta_1/\alpha_1$ 850-nm wavelength signal component=$b_2 c_2 \times$
$c\_{FD2} = b_2 c_2/\alpha_1$ Leakage component=$c_2$ The signal processing circuit 115 acquires the signals $a_2$, $b_2$, and $c_2$ from the image sensor 113, acquires the coefficients $\alpha_1$ and $\beta_1$ from the second memory, and performs the calculation of the above formula to thereby correct the signals of the floating diffusion layer 406 and the floating diffusion layer 404.

In the $n+2^{th}$ frame period, the 750-nm wavelength signal component, the 850-nm wavelength signal component, and the leakage component are expressed by means of the following formulas.

750-nm wavelength signal component=$a_3 - c_3 \times/$
$c\_{FD2}/c\_{FD1} = a_3 - c_3 \times \alpha_1$ 850-nm wavelength signal component=$b_3 - c_3 \times/$
$c\_{FD3}/c\_{FD1} = b_3 - c_3 \times \beta_1$ Leakage component=$c_3$ The signal processing circuit 115 acquires the signals $a_3$, $b_3$, and $c_3$ from the image sensor 113, acquires the coefficients $\alpha_1$ and $\beta_1$ from the second memory, and performs the calculation of the above formula to thereby correct the signals of the floating diffusion layer 405 and the floating diffusion layer 406.

Hereinafter, in each of the $n+3^{th}$ to $n+5^{th}$ frame periods, the signal processing circuit 115 corrects signals using calculation formulas similar to those for the $n^{th}$ to $n+2^{th}$ frame periods. Thereafter, likewise, signals are corrected with three types of calculation formulas being applied in sequence in each frame period. In this way, in the present embodiment, the driving method for the floating diffusion 404, the floating diffusion layer 405, and the floating diffusion layer 406 is rotated, and thus the calculation for obtaining the signal component of each wavelength is also rotated.

As mentioned above, signals can be corrected by performing the aforementioned calculations. However, if the target object 102 moves between frame periods, the way in which surface reflected light is incident changes, and therefore the distribution of leakage components can change. In such a case, correct signals cannot be obtained if the coefficients $\alpha_1$ and $\beta_1$ in effect up to that point in time are applied. Thus, in the present embodiment, the signal processing circuit 115 detects motion of the target object 102, and updates coefficients at the next stationary timing if motion is detected. The detection of motion of the target object 102 can be carried out for each pixel or for each adjacent pixel group, for example. The method for detecting motion is not restricted to a specific method and may be any method. For example, the signal processing circuit 115 may detect motion in an individual pixel of the target object 102 by comparing the amount of change per time of a luminance value in that pixel and a predetermined threshold value. Alternatively, the signal processing circuit 115 may calculate a motion vector for the target object 102 in a pixel group having a pixel of interest at the center thereof, and may determine that the target object 102 is moving in the case where the magnitude of said motion vector is greater than a predetermined threshold value.

In the example depicted in FIG. 15, when a signal is generated in the $n^{th}$ frame period for example, the signals $a_1$, $b_1$, and $c_1$ of the three floating diffusion layers in each pixel are input to the signal processing circuit 115 and recorded in the first memory, which is a frame memory. The signal processing circuit 115 reads the signals $a_0$, $b_0$, and $c_0$ of the immediately preceding frame period already recorded in the frame memory. The signal processing circuit 115 compares the signals $a_1$, $b_1$, and $c_1$ of the $n^{th}$ frame period and the signals $a_0$, $b_0$, and $c_0$ of the immediately preceding frame period, and determines whether or not the target object 102 has moved between the two consecutive frame periods. The signal processing circuit 115 performs the same operation also for the frame periods thereafter, and, for each frame period, determines whether or not the target object 102 has moved.

In the example depicted in FIG. 15, motion of the target object 102 has been detected up to the $n+2^{th}$ frame period, but in the $n+3^{th}$ frame period, it is detected that the target object 102 has not moved since the $n+2^{th}$ frame period and is stationary. Likewise, in the $n+7^{th}$ frame period, it is detected that the target object 102 has not moved since the $n+6^{th}$ frame period. Therefore, when generating the $n+3^{th}$ frame period, the signal processing circuit 115 performs the calculation $\alpha_2 = C2/C3$, and updates the coefficient $\alpha_1$ that has been in effect up to that point in time to $\alpha_2$ and records this in the second memory. Likewise, when generating a signal in the $n+7^{th}$ frame period, the signal processing circuit 115 performs the calculation $\beta_2 = C7/C6$, and updates the coefficient $\beta_1$ that has been in effect up to that point in time to $\beta_2$ and records this in the second memory. Once the coefficients are updated, the signal processing circuit 115 subsequently uses the updated coefficients to calculate signal components for each of the 750-nm and 850-nm wavelengths.

The above description has been given with processing for the second frame period and thereafter being assumed; however, the same processing can also be applied to the first frame period. The coefficients $\alpha$ and $\beta$ used in the first frame period can be determined from the ratio of leakage components inspected at the time of factory dispatch, for example. Initial values of such coefficients are recorded in the second memory of the signal processing circuit 115 in advance.

The first light source 103 and the second light source 104 are used in the present embodiment; however, the same operation may be carried out using only either one of the light sources. In such a case, there may be two or more floating diffusion layers, and the roles of the two floating diffusion layers may be switched in an alternating manner in two consecutive frame periods. For example, a configuration in which the light source 104 and the floating diffusion layer 405 have been excluded from the configuration of the present embodiment is feasible. In such a configuration, the control circuit 114 performs the following operation, for example, for the first and second frame periods that are consecutive.

<First Frame Period>

(1) In a period that includes a period in which the first light source 103 is made to emit pulsed light, and the surface reflected component from within the pulsed light emitted from the first light source 103 is incident on the image sensor 113, a state is implemented in which signal charge is discharged, and the floating diffusion layer 406 is made to accumulate the signal charge that has remained without being discharged to the drain 402, from within the signal charge generated by the photoelectric conversion element. (2) In a period in which, from within the pulsed light emitted from the first light source 103, the internally scattered component is incident on the image sensor 113 after the trailing end of the surface reflected component has been incident on the image sensor 113, a state is implemented in which the signal charge is accumulated in the floating diffusion layer 404 without being discharged to the drain 402, and the floating diffusion layer 404 is made to accumulate the signal charge. (3) After the accumulation of the signal charge to the floating diffusion layers 404 and 406 has completed, the image sensor 113 is made to generate a first signal that is based on the signal charge accumulated in the floating diffusion layer 404, and a second signal that is based on the signal charge accumulated in the floating diffusion layer 406.

<Second Frame Period>

(4) In a period that includes a period in which the first light source 103 is made to emit pulsed light, and the surface reflected component from within the pulsed light emitted from the first light source 103 is incident on the image sensor 113, a state is implemented in which signal charge is discharged, and the floating diffusion layer 404 is made to accumulate signal charge that has remained without being discharged to the drain 402, from within the signal charge generated by the photoelectric conversion element. (5) In a period in which, from within the pulsed light emitted from the first light source 103, the internally scattered component is incident on the image sensor 113 after the trailing end of the surface reflected component has been incident on the image sensor 113, a state is implemented in which signal charge is accumulated in the floating diffusion layer 406 without being discharged to the drain 402, and the floating diffusion layer 406 is made to accumulate the signal charge. (6) After the accumulation of the signal charge to the floating diffusion layer 404 and the floating diffusion layer 406 has completed, the image sensor 113 is made to generate a third signal that is based on the signal charge accumulated in the floating diffusion layer 404, and a fourth signal that is based on the signal charge accumulated in the floating diffusion layer 406.

The signal processing circuit 115 can calculate a signal value for each pixel of a frame in the second frame period by subtracting a signal obtained by multiplying the third signal by a precalculated coefficient (corresponding to the aforementioned $\beta$), from the fourth signal, for each pixel.

In the third frame period subsequent to the second frame period, the same operation as in the first frame period is once again carried out. However, in the third frame period, the signal processing circuit 115 calculates a signal value for each pixel by subtracting a signal obtained by multiplying the second signal by a precalculated coefficient (corresponding to $1/\beta$), from the first signal, for each pixel. Furthermore, the signal processing circuit 115 may detect motion of the target object 102 in each pixel on the basis of frame data, and when no motion of the target object 102 has been detected, the coefficients may be updated using at least one of the first to fourth signals. It is thereby possible to perform detection with a high degree of accuracy even in the case where the target object 102 has moved.

According to the above processing, in the present embodiment, the internally scattered component of light from the target object 102 in each pixel can be detected with a high degree of accuracy in each frame period. The leakage component can be correctly eliminated from the signal components accumulated in the floating diffusion layers, even in the case where a deviation occurs in the leakage component distribution in the floating diffusion layers. According to the present embodiment, it is possible to use a comparatively inexpensive non-telecentric optical system 111, and it is not necessary for the plurality of floating diffusion layers to be arranged isotropically from the photodiode. Therefore, the degree of freedom in the design for the imaging device 101 can be increased. Furthermore, it is not necessary for a calibration frame to be provided as in embodiment 2, and it is therefore possible for the frame rate to be further increased.

Embodiment 4

Next, the imaging device 101 of embodiment 4 will be described. The present embodiment is different from embodiment 3 in that it is possible to simultaneously detect a background light component in addition to a leakage component of light. The present embodiment is the same as embodiment 3 in that the combination of the two floating diffusion layers for detecting the internally scattered component and the floating diffusion layer for detecting the leakage component is changed in each frame period. By detecting the background light component in addition to the leakage component, it is possible to accurately eliminate the leakage component and the background light component from a signal. Hereinafter, a description will be given focusing on the difference with embodiment 3.

When using the imaging device 101, it is common for background light caused by the environment such as lighting and natural light to be present as well as the pulsed light emitted from the first light source 103 and the second light source 104. There are cases where this kind of background light includes components having the same wavelength as the wavelength of the pulsed light emitted from the first light source 103 and the second light source 104. In such a case, even if the double bandpass filter 112 is arranged opposing the imaging surface of the image sensor 113, there is a risk of background light being incident on the image sensor 113 and noise being generated. Thus, in the present embodiment, a period in which the background light component is detected in addition to the leakage component is provided in each frame period.

Figure 16A:
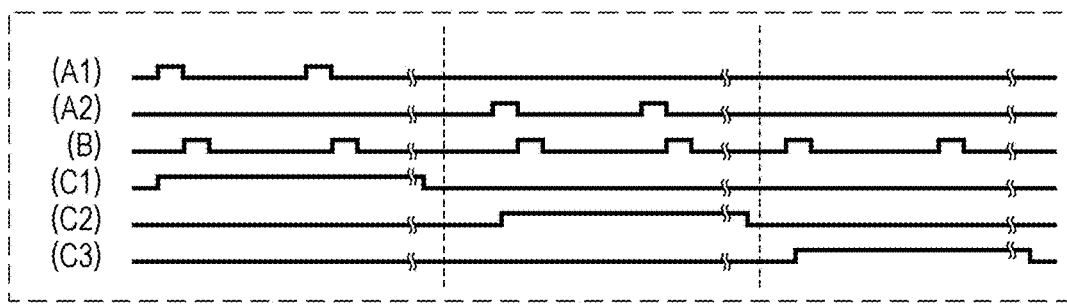
FIG. 16A is a timing chart depicting an operation in a first frame period in embodiment 4.
Figure 16B:
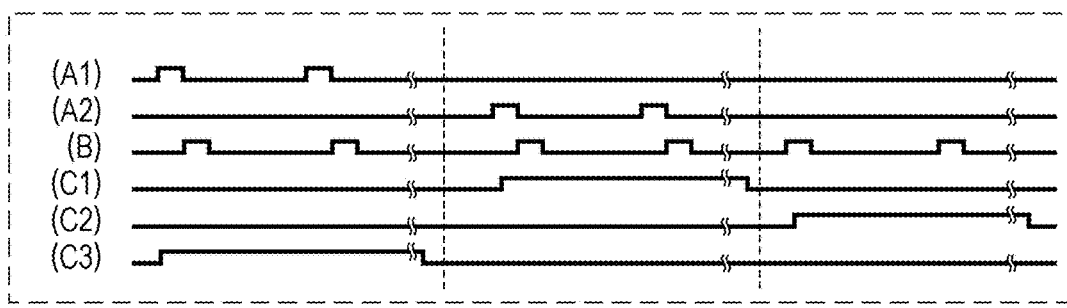
FIG. 16B is a timing chart depicting an operation in a second frame period in embodiment 4.
Figure 16C:
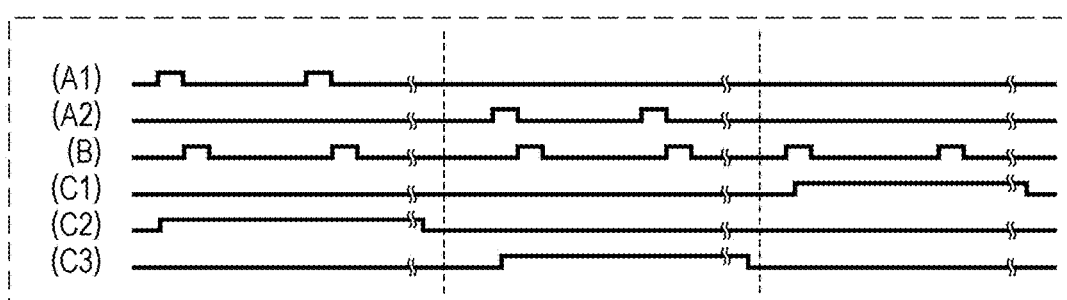
FIG. 16C is a timing chart depicting an operation in a third frame period in embodiment 4.

FIGS. 16A to 16C are timing charts depicting operations in the present embodiment. FIG. 16A is a timing chart depicting an operation in the first frame period. FIG. 16B is a timing chart depicting an operation in the second frame period. FIG. 16C is a timing chart depicting an operation in the third frame period. The operations depicted in FIGS. 16A to 16C are sequentially repeated in the fourth frame period and thereafter.

In the present embodiment, compared with embodiment 3, when a signal in each frame period is to be acquired, after a period in which signal charge caused by 750-nm laser pulsed light is accumulated and a period in which signal charge caused by 850-nm laser pulsed light is accumulated have ended, a period for acquiring the background light component is added. In said period, the first light source 103 and the second light source 104 are set to a non-emission state, only one of the floating diffusion layers 404, 405, and 406 is set to be active, and the electronic shutter is opened and closed in a manner similar to other periods.

In the first frame period, after the 750-nm light emission period and the 850-nm light emission period have ended, the first light source 103 and the second light source 104 are set to a non-emission state, only the floating diffusion layer 406 is set to be active, and the electronic shutter is opened at the same time as the control time for the electronic shutter in a period in which the floating diffusion layer 404 or the floating diffusion layer 405 is active, and for the same number of times. Thus, a background light component of approximately the same amount as a background light component accumulated in the floating diffusion layer 404 or the floating diffusion layer 405 is accumulated in the floating diffusion layer 406. The operation in the period during which the first light source 103 and the second light source 104 are emitting light is the same as the operation of FIG. 13A in embodiment 3.

In the second frame period, after the 750-nm light emission period and the 850-nm light emission period have ended, the first light source 103 and the second light source 104 are set to a non-emission state, only the floating diffusion layer 405 is set to be active, and the electronic shutter is opened at the same time as the control time for the electronic shutter in a period in which the floating diffusion layer 404 or the floating diffusion layer 406 is active, and for the same number of times. Thus, a background light component of approximately the same amount as a background light component accumulated in the floating diffusion layer 404 or the floating diffusion layer 406 is accumulated in the floating diffusion layer 405. The operation in the period during which the first light source 103 and the second light source 104 are emitting light is the same as the operation of FIG. 13B in embodiment 3.

In the third frame period, after the 750-nm light emission period and the 850-nm light emission period have ended, the first light source 103 and the second light source 104 are set to a non-emission state, only the floating diffusion layer 404 is set to be active, and the electronic shutter is opened at the same time as the control time for the electronic shutter in a period in which the floating diffusion layer 405 or the floating diffusion layer 406 is active, and for the same number of times. Thus, a background light component of approximately the same amount as a background light component accumulated in the floating diffusion layer 405 or the floating diffusion layer 406 is accumulated in the floating diffusion layer 404. The operation in the period during which the first light source 103 and the second light source 104 are emitting light is the same as the operation of FIG. 13C in embodiment 3.

The method for calculating the 750-nm signal amount and the 850-nm signal amount from the signal amount included in the floating diffusion layers is the same as the method in embodiment 3, and therefore a description thereof has been omitted.

It should be noted that it is not necessary for the period in which the background light component is acquired to be after the first light source 103 and second light source 104 light emission periods have ended. The background light component may be acquired before the first light source 103 and second light source 104 light emission periods, or between the first light source 103 and second light source 104 light emission periods.

As mentioned above, the control circuit 114 in the present embodiment, in each frame period, causes an accumulation unit that detects the leakage component in surface reflected light to accumulate signal charge caused by the surface reflected component of pulsed light, and, in a period in which no pulsed light is incident on the image sensor 113 (for example, after the emission of pulsed light has ended), implements a state in which the signal charge is not discharged, and causes said accumulation unit to further accumulate the signal charge.

According to the above processing, it is possible to eliminate not only the leakage component of surface reflected light but also the background light component from a detected signal. It is therefore possible for the internally scattered component in each pixel to be detected with an even higher degree of accuracy. In the present embodiment also, the leakage component can be correctly eliminated from the signal components accumulated in each FD, even in the case where a deviation occurs in the leakage component distribution in the floating diffusion layers. According to the present embodiment, it is possible to use a comparatively inexpensive non-telecentric optical system 111, and it is not necessary for the plurality of floating diffusion layers to be arranged isotropically from the photodiode. Therefore, the degree of freedom in the design for the imaging device 101 can be increased. Furthermore, it is not necessary for a calibration frame to be provided as in embodiment 2, and it is therefore possible for the frame rate to be further increased.

In the present embodiment, the combination of the floating diffusion layer for detecting the internally scattered component and the floating diffusion layer for detecting the leakage component is rotated in each frame period, similar to embodiment 3; however, it should be noted that a calibration frame period in which none of the floating diffusion layers are set to be active may be provided, similar to embodiment 2. In such a case, processing that is the same as the signal processing in embodiment 2 can be applied to acquire a biological signal.

Embodiment 5

Next, the imaging device 101 of embodiment 5 will be described. The present embodiment is common with embodiment 4 in that a background light component is simultaneously detected in addition to a leakage component of surface reflected light, but the timing at which the background light component is detected is different from that in embodiment 4. The present embodiment is the same as embodiment 3 in that the combination of the two floating diffusion layers for detecting the internally scattered component and the floating diffusion layer for detecting the leakage component is changed in each frame period. By detecting the background light component in addition to the leakage component, it is possible to accurately eliminate the leakage component and the background light component from a detected signal. Hereinafter, a description will be given focusing on the difference with embodiment 4.

Figure 17A:
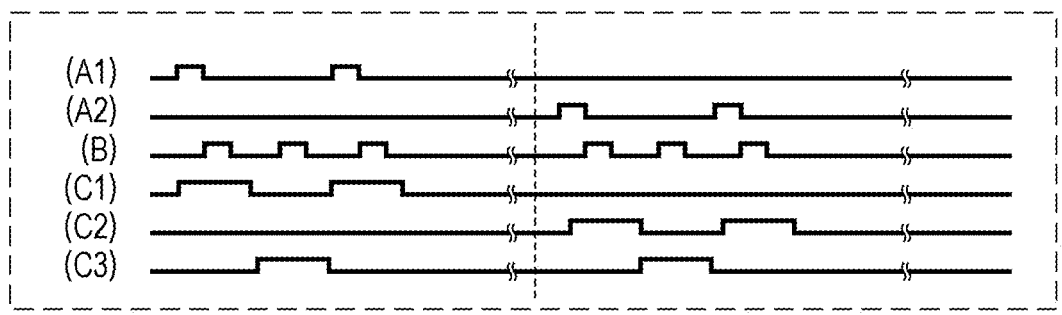
FIG. 17A is a timing chart depicting an operation in a first frame period in embodiment 5.
Figure 17B:
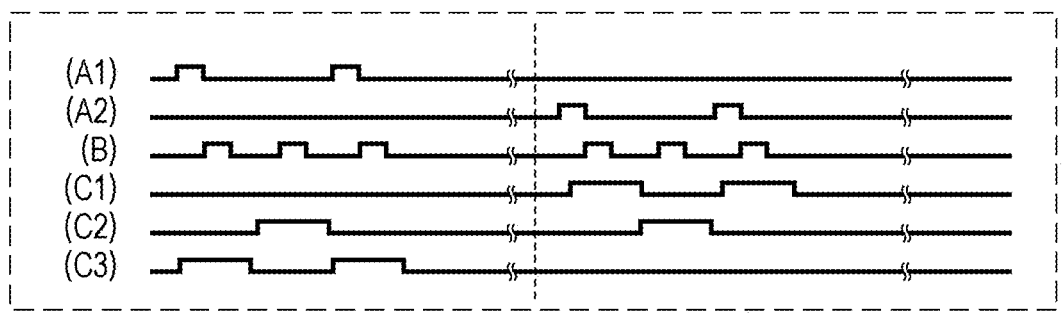
FIG. 17B is a timing chart depicting an operation in a second frame period in embodiment 5.
Figure 17C:
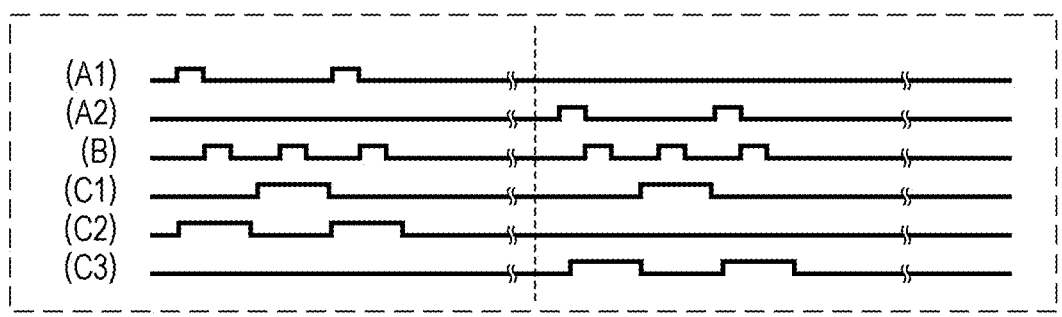
FIG. 17C is a timing chart depicting an operation in a third frame period in embodiment 5.

FIGS. 17A to 17C are timing charts depicting operations in the present embodiment. FIG. 17A is a timing chart depicting an operation in the first frame period. FIG. 17B is a timing chart depicting an operation in the second frame period. FIG. 17C is a timing chart depicting an operation in the third frame period. The operations depicted in FIGS. 17A to 17C are sequentially repeated in the fourth frame period and thereafter.

As is apparent from FIGS. 17A to 17C, in the present embodiment, the operation for accumulating the background light component carried out last in each frame period in embodiment 4 is carried out at a timing in the middle of two consecutive emissions of pulsed light. By increasing the speed of control of the floating diffusion layers, the background light component and the leakage component, similar to the internally scattered component, can be acquired at approximately the same timing as a light-emission pulse. The time taken to acquire the background light component is shortened compared to embodiment 4, and therefore the frame rate can be improved.

As mentioned above, in the present embodiment, signal charge of the background light component is accumulated while each of the first light source 103 and the second light source 104 are made to generate two consecutive instances of pulsed light (first and second pulse light). After the incidence of the first pulsed light onto the image sensor 113 has ended, before the incidence of the second pulsed light to the image sensor 113 starts, the control circuit 114 implements a state in which signal charge is not discharged, and causes the accumulation unit that detects the leakage component to further accumulate the signal charge. The signal processing circuit 115 carries out processing similar to that in embodiments 3 and 4, and eliminates the leakage component and the background light component from signals caused by the internally scattered component.

According to the above operation, an effect that is similar to that of embodiment 4 can be obtained. In addition, the frame rate can be increased compared to that in embodiment 4.

Embodiment 6

Next, the imaging device 101 of embodiment 6 will be described. In the present embodiment, electronic shutter periods having two different phases are provided for one emission of light, and signal charge is accumulated in respectively different floating diffusion layers. Thus, information regarding scalp blood flow in a superficial section of the target object 102 and information regarding cerebral blood flow in a deep section can be detected separately with a high degree of accuracy.

Figure 18:
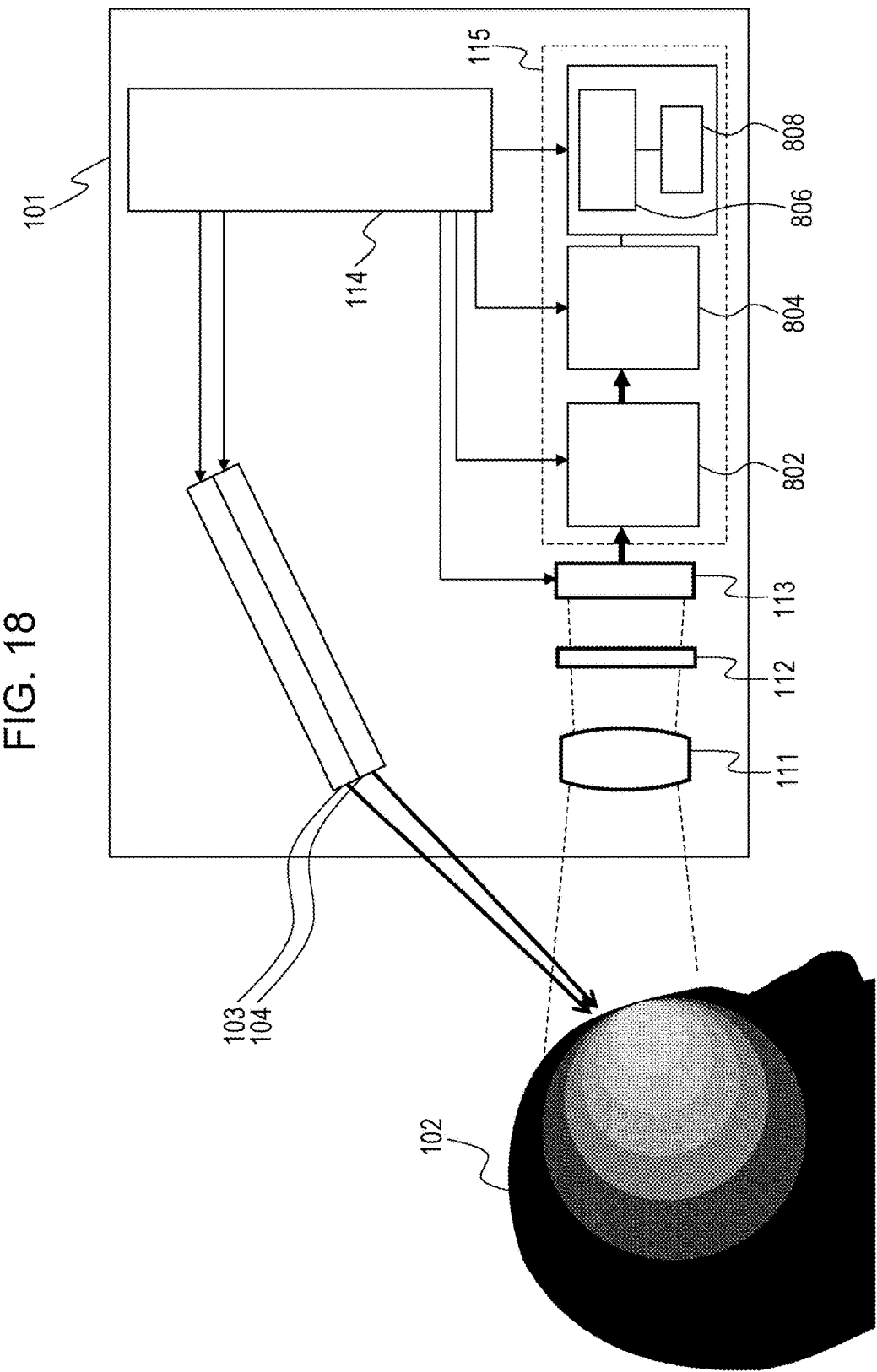
FIG. 18 is a drawing depicting a configuration of an imaging device in embodiment 6.

FIG. 18 is a drawing depicting a configuration of the imaging device 101 of the present embodiment. In the present embodiment, the configuration of the pixels of the image sensor 113 and the operation of the signal processing circuit 115 are different from that in embodiment 5. Hereinafter, a description will be given focusing on the differences with embodiment 5.

The signal processing circuit 115 in the present embodiment includes: a first circuit 802 that performs processing to separate information regarding a superficial section and a deep section of the target object 102; a second circuit 804 that performs processing to generate image data; a motion detection circuit 806 that executes motion detection processing; and a memory 808. From thereamong, processing is similar to that in embodiment 5 apart from the processing to separate information regarding a superficial section and a deep section of the target object 102.

Figure 19:
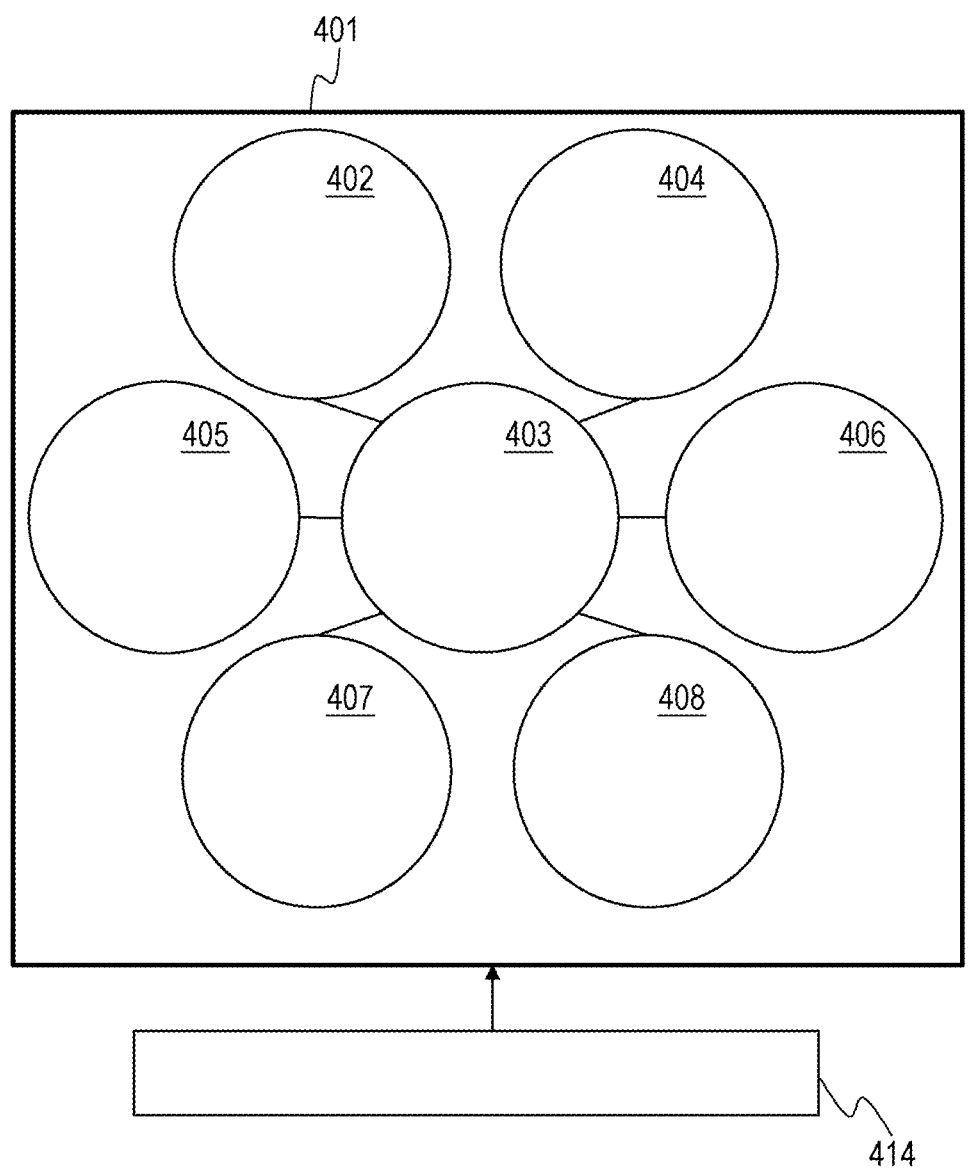
FIG. 19 is a drawing schematically depicting a pixel configuration of an image sensor in embodiment 6.

FIG. 19 is a drawing schematically depicting a pixel configuration of the image sensor 113 in the present embodiment. Each pixel of the image sensor 113 in the present embodiment has five floating diffusion layers 404, 405, 406, 407, and 408. In order to acquire information regarding a superficial section and a deep section of a living body independently for each wavelength, two floating diffusion layers are provided for each of the first light source 103 and the second light source 104. It should be noted that, in the present embodiment, it is not necessary for the floating diffusion layers 404, 405, 406, 407, and 408 to be arranged isotropically from the photodiode 403 since the control described in relation to embodiment 3 is carried out.

Figure 20:
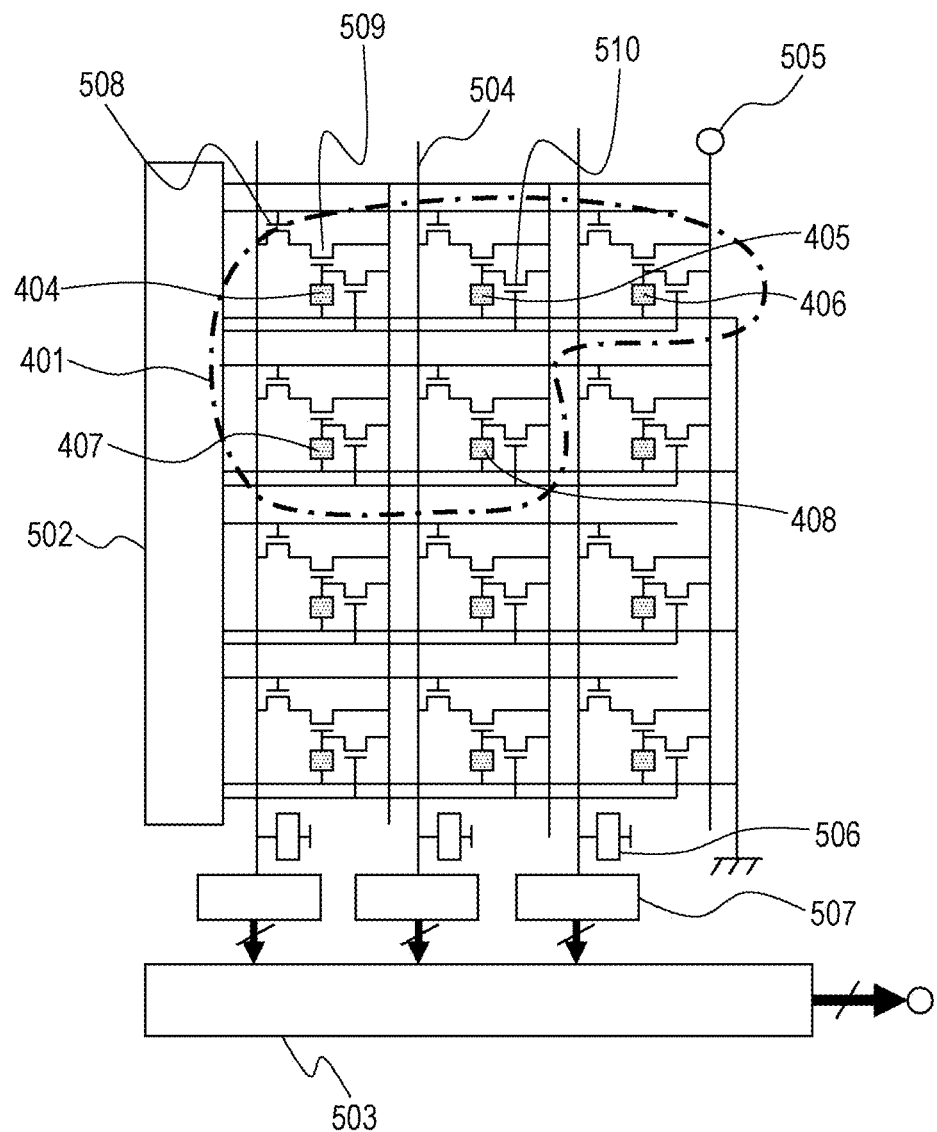
FIG. 20 is a drawing schematically depicting an example of a configuration of the image sensor in embodiment 6.

FIG. 20 is a drawing schematically depicting an example of a configuration of the image sensor 113. In FIG. 20, the region surrounded by the one-dot chain line corresponds to one pixel 401. The pixel 401 includes the five floating diffusion layers 404, 405, 406, 407, and 408. Signals accumulated in the five floating diffusion layers 404, 405, 406, 407, and 408 are treated as if they were signals of five pixels of a general CMOS image sensor, and are output from the image sensor 113. It should be noted that FIG. 20 depicts only elements relating to an operation in which the signal charge inside the floating diffusion layers 404, 405, 406, 407, and 408 is output from the image sensor 113 once the accumulation of the signal charge has completed in each of the floating diffusion layers 404, 405, 406, 407, and 408 (referred to as a "low-speed reading operation"). The drain 402, the photodiode 403, and the high-speed timing control circuit 414 are not directly related to the low-speed reading operation, and have therefore been omitted from FIG. 20.

Figure 21A:
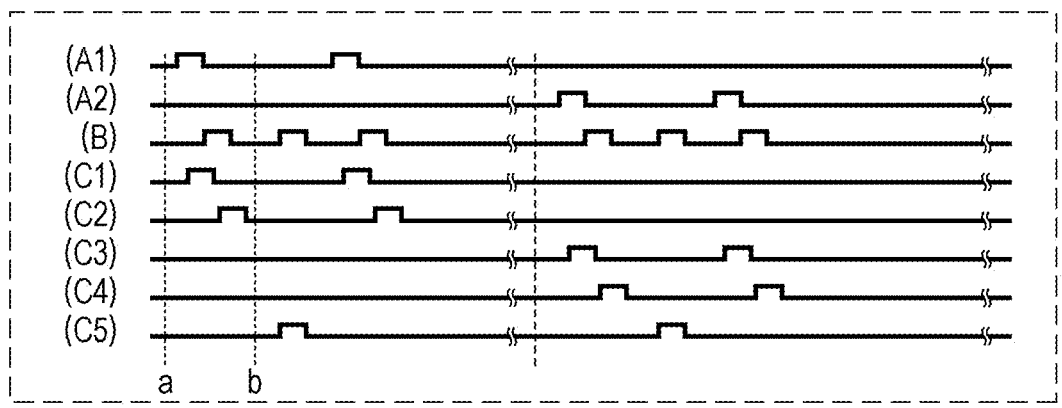
FIG. 21A depicts system timings in a first frame period in embodiment 6.
Figure 21B:
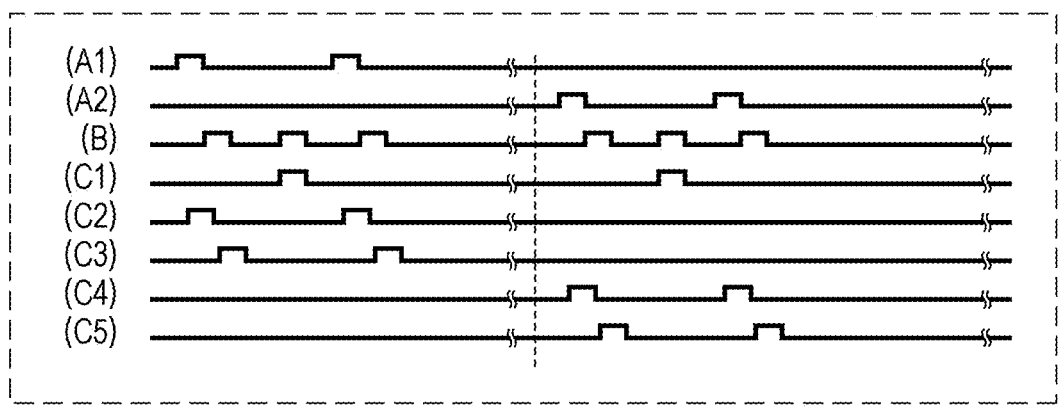
FIG. 21B depicts system timings in a second frame period in embodiment 6.
Figure 21C:
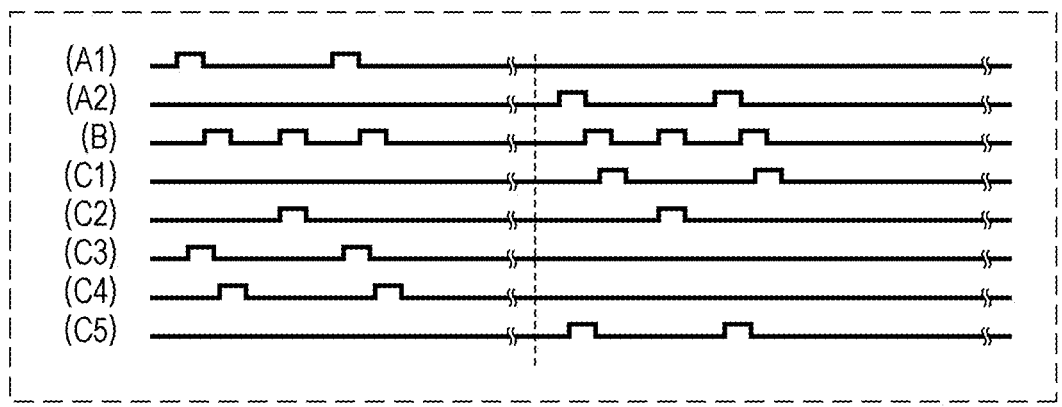
FIG. 21C depicts system timings in a third frame period in embodiment 6.
Figure 21D:
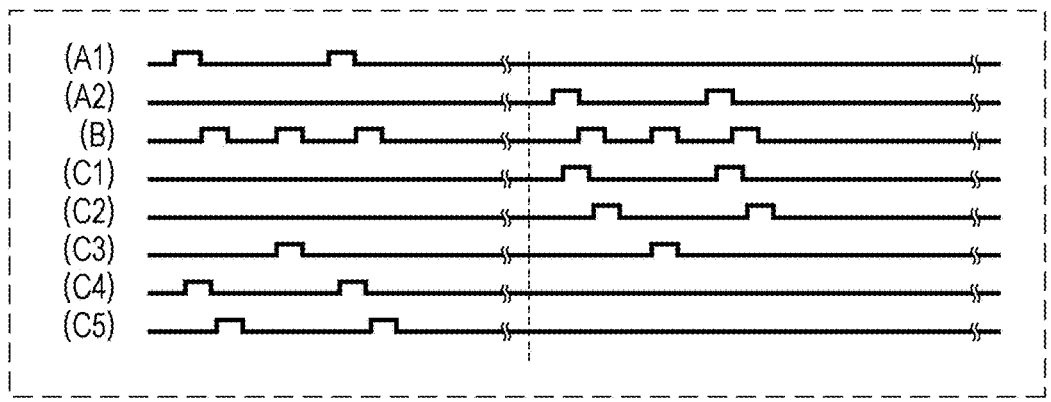
FIG. 21D depicts system timings in a fourth frame period in embodiment 6.
Figure 21E:
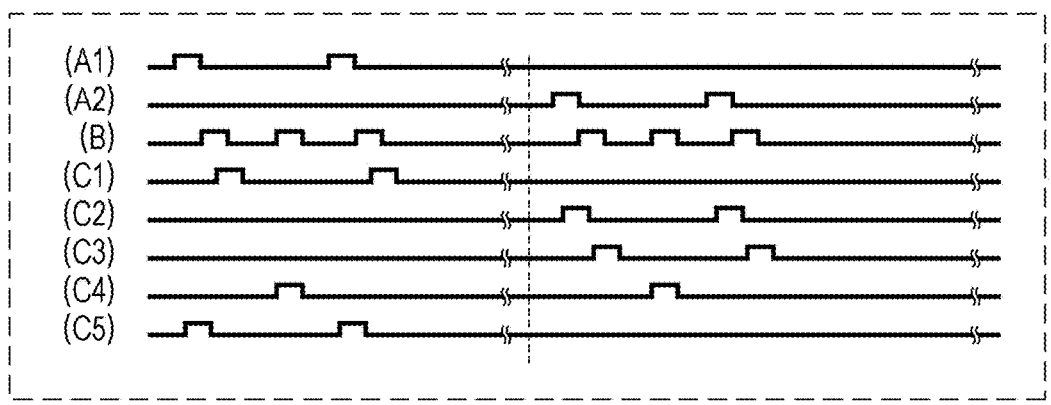
FIG. 21E depicts system timings in a fifth frame period in embodiment 6.

FIGS. 21A to 21E are timing charts depicting a control method in the present embodiment. In FIGS. 21A to 21E, signals A1 and A2 respectively indicate waveforms of pulsed light emitted from the first light source 103 and the second light source 104, signal B indicates the opening and closing timings of the electronic shutter, and signals C1, C2, C3, C4, and C5 respectively indicate the on timings (in other words, the state in which charge is accumulated in the floating diffusion layers) and the off timings (in other words, the state in which charge is not accumulated in the floating diffusion layers) of the floating diffusion layers 404, 405, 406, 407, and 408. FIG. 21A depicts system timings in a first frame period. FIG. 21B depicts system timings in a second frame period. FIG. 21C depicts system timings in a third frame period. FIG. 21D depicts system timings in a fourth frame period. FIG. 21E depicts system timings in a fifth frame period. The operations depicted in FIGS. 21A to 21E are sequentially repeated in the sixth frame period and thereafter. As is apparent from FIGS. 21A to 21E, in the present embodiment, the roles of the floating diffusion layers 404, 405, 406, 407, and 408 are sequentially changed in each frame period.

In the first frame period depicted in FIG. 21A, the internally scattered component of pulsed light having a central wavelength of 750 nm is detected by the floating diffusion layers 404 and 405. The internally scattered component of pulsed light having a central wavelength of 850 nm is detected by the floating diffusion layers 406 and 407. The leakage component and the background light component of the surface reflected light are detected by the floating diffusion layer 408.

In the second frame period depicted in FIG. 21B, the internally scattered component of pulsed light having a central wavelength of 750 nm is detected by the floating diffusion layers 405 and 406. The internally scattered component of pulsed light having a central wavelength of 850 nm is detected by the floating diffusion layers 407 and 408. The leakage component and the background light component of the surface reflected light are detected by the floating diffusion layer 404.

In the third frame period depicted in FIG. 21C, the internally scattered component of pulsed light having a central wavelength of 750 nm is detected by the floating diffusion layers 406 and 407. The internally scattered component of pulsed light having a central wavelength of 850 nm is detected by the floating diffusion layers 404 and 408. The leakage component and the background light component of the surface reflected light are detected by the floating diffusion layer 405.

In the fourth frame period depicted in FIG. 21D, the internally scattered component of pulsed light having a central wavelength of 750 nm is detected by the floating diffusion layers 407 and 408. The internally scattered component of pulsed light having a central wavelength of 850 nm is detected by the floating diffusion layers 404 and 405. The leakage component and the background light component of the surface reflected light are detected by the floating diffusion layer 406.

In the fifth frame period depicted in FIG. 21E, the internally scattered component of pulsed light having a central wavelength of 750 nm is detected by the floating diffusion layers 404 and 408. The internally scattered component of pulsed light having a central wavelength of 850 nm is detected by the floating diffusion layers 405 and 406. The leakage component and the background light component of the surface reflected light are detected by the floating diffusion layer 407.

The specific operation in each frame period is the same as the operation in embodiment 5 apart from the point that the number of floating diffusion layers controlled in synchronization with the emission of light by the light sources is increased to two.

Figure 22A:
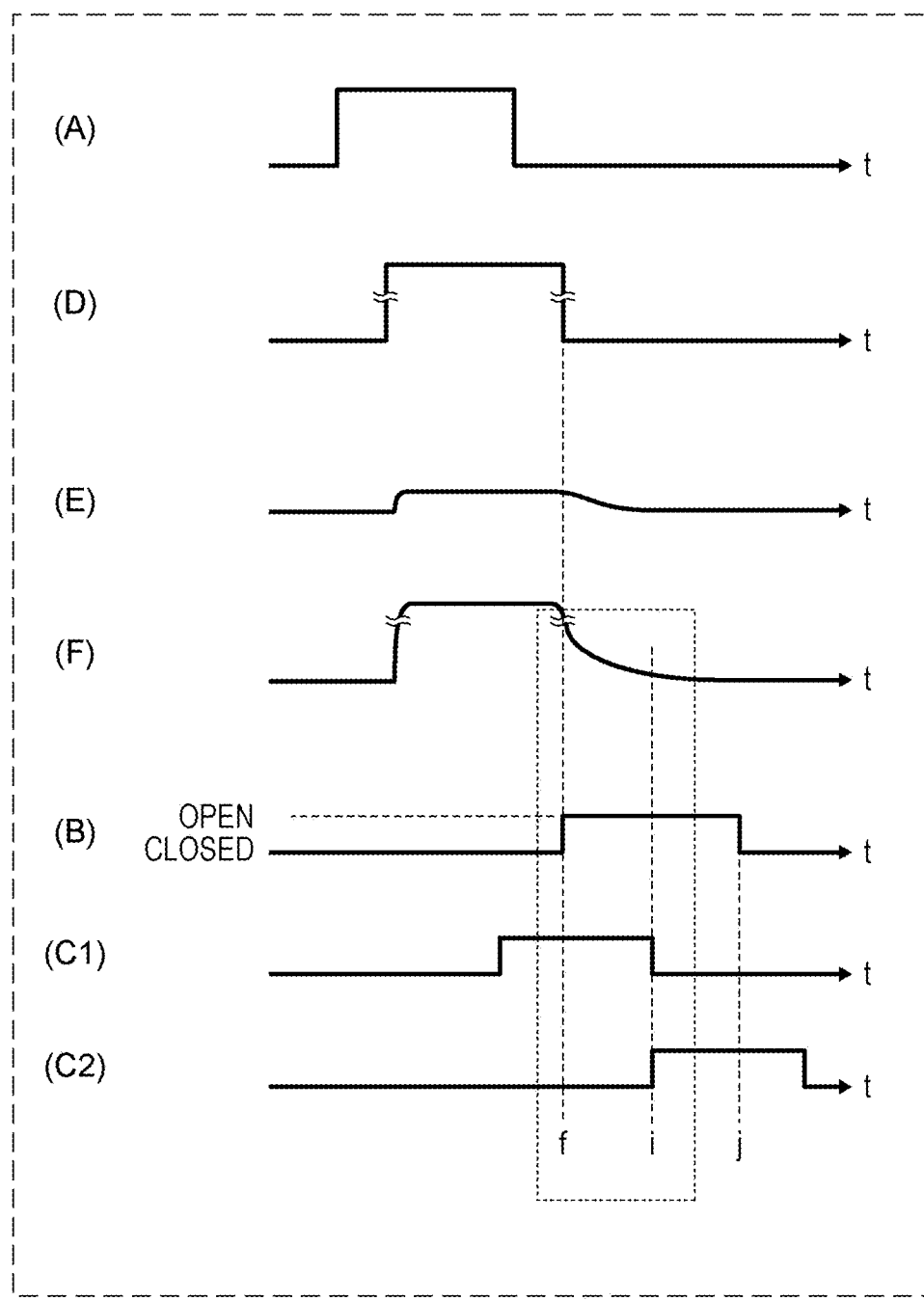
FIG. 22A is a drawing depicting, in more detail, the operation from time a to time b depicted in FIG. 21A.
Figure 22B:
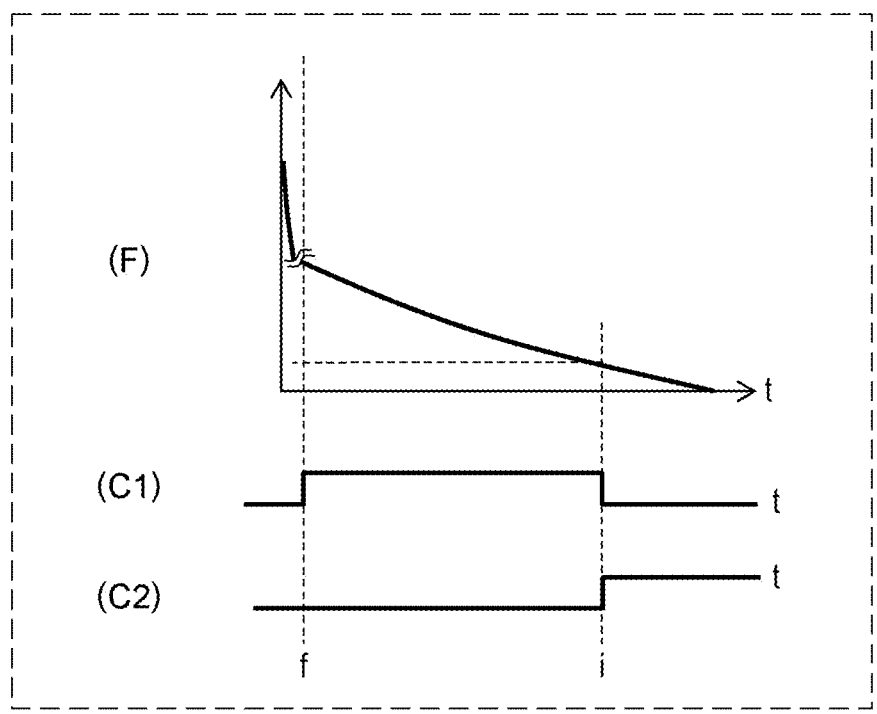
FIG. 22B is a drawing depicting an enlarged view of the interior of the dotted border in FIG. 22A.

FIG. 22A is a drawing depicting, in more detail, the operation from time a to time b depicted in FIG. 21A. FIG. 22B is a drawing depicting an enlarged view of the interior of the dotted border in FIG. 22A.

In FIGS. 22A and 22B, signal A indicates the waveform of pulsed light that is emitted from the first light source 103. Signal D indicates, from within the pulsed light, the waveform of the surface reflected component l1 that is reflected by the surface of the target object 102 and returned. Signal E indicates, from within the pulsed light, the waveform of the internally scattered component l2 that is scattered inside the target object 102 and returned. Signal F indicates a waveform in which the surface reflected component l1 and the internally scattered component l2 are combined. Signal B indicates the opening and closing timings of the electronic shutter. Signals C1 and C2 respectively indicate the on timings (in other words, the state in which charge is accumulated in the floating diffusion layers) and the off timings (in other words, the state in which charge is not accumulated in the floating diffusion layers) of the floating diffusion layers 404 and 405.

As is apparent from these drawings, in the present embodiment, the electronic shutter is switched from closed to open at time f, which is the timing at which the surface reflected component of pulsed light disappears. The open period is maintained for a period equivalent to the light-emission pulse width, and at time j, the electronic shutter is once again switched to closed. At such time, the floating diffusion layer 404 is already active when the shutter is open, and is set to be inactive at time i, which is the midpoint while the shutter is open. The floating diffusion layer 405 is set to be active at the same time as the floating diffusion layer 404 becomes inactive. The floating diffusion layer 405 continues to be in an active state until the timing at which the shutter closes, and thereafter is set to be inactive. The first light source 103 repeatedly emits pulsed light, and therefore the electronic shutter, the floating diffusion layer 404, and the floating diffusion layer 405 are also controlled in synchronization with the emission of light.

In the period depicted in FIG. 22A, the floating diffusion layers 406, 407, and 408 are inactive. Thus, the signal charge from time f to time i, namely the first half of the period in which the electronic shutter is open, is accumulated in the floating diffusion layer 404, and the signal charge from time i to time j, namely the second half, is accumulated in the floating diffusion layer 405. Therefore, the signal charge in the floating diffusion layer 404 includes far more components caused by light from the scalp constituting the superficial section of the target object 102, than components caused by light from the brain constituting the deep section of the target object 102. On the other hand, in the signal charge in the floating diffusion layer 405, although less than the components caused by light from the scalp constituting the superficial section of the target object 102, the proportion of components caused by light from the brain constituting the deep section of the target object 102 is comparatively large.

By causing the floating diffusion layers 404 and 405 to respectively accumulate signal charge in a divided manner in the first half and second half of an open period of the electronic shutter, the ratio between the components of the superficial section and the components of the deep section can be made to be different between the floating diffusion layer 404 and the floating diffusion layer 405.

The above operation is the same also in a period in which the second light source 104 that emits pulsed light having a central wavelength of 850 nm is driven, apart from the point that the pair of floating diffusion layers used is different. In the period in which the second light source 104 is driven in the first frame period, the floating diffusion layers 404, 405, and 408 are inactive. Thus, the signal charge of the first half of the period in which the electronic shutter is open is accumulated in the floating diffusion layer 406, and the signal charge of the second half is accumulated in the floating diffusion layer 407. Therefore, the signal charge in the floating diffusion layer 406 includes far more components caused by light from the scalp constituting the superficial section of the target object 102, than components caused by light from the brain constituting the deep section of the target object 102. On the other hand, in the signal charge in the floating diffusion layer 407, although less than the components caused by light from the scalp constituting the superficial section of the target object 102, the proportion of components caused by light from the brain constituting the deep section of the target object 102 is comparatively large.

As depicted in FIG. 21A, in the first frame period, the floating diffusion layer 408 is set to be on in a period in which 750-nm light and 850-nm light are extinguished from the image sensor 113. During this time, the floating diffusion layers 404, 405, 406, and 407 are set to be off, and therefore the signal charge generated by photoelectric conversion by the photodiode is accumulated in the floating diffusion layer 408. In other words, the background light component is included in a signal from the floating diffusion layer 408. It should be noted that the exposure time and number of exposures of the floating diffusion layer 408 is equal to the exposure time and number of exposures of each of the floating diffusion layers 404, 405, 406, and 407.

The operations in the other frame periods depicted in FIGS. 21B to 21D are the same as the operation in the first frame period apart from the point that the combination of the three floating diffusion layers set to be active is different, and therefore a description thereof has been omitted. Furthermore, the method for calculating the signal amount of the internally scattered component of 750-nm light and the signal amount of the internally scattered component of 850-nm light on the basis of the signals obtained from the floating diffusion layers can be executed with the same approach as the method in embodiment 3 (for example, FIG. 15), and therefore a description thereof has been omitted.

As mentioned above, in the present embodiment, in addition to the effect of embodiment 5, it is possible to obtain a signal in which the proportion of components of a deep section of a living body is relatively large and a signal in which said proportion is relatively small for each light source. Therefore, the signal processing circuit 115 can generate a signal indicating the state of scalp blood flow and a signal indicating the state of cerebral blood flow on the basis of both signals.

In the present embodiment, the combination of the floating diffusion layer for detecting the internally scattered component and the floating diffusion layer for detecting the leakage component is rotated in each frame period, similar to embodiment 3; however, it should be noted that a calibration frame in which none of the floating diffusion layers are set to be active may be provided, similar to embodiment 2. In such a case, processing that is the same as the signal processing in embodiment 2 can be applied to acquire a biological signal.

Embodiment 7

Next, the imaging device 101 of embodiment 7 will be described. In the present embodiment, the case where the image sensor 113 is a CCD type will be specifically described. In the present embodiment, signal charge is read from the photodiode by setting the potential of a specific floating diffusion layer to be relatively low compared to that of other floating diffusion layers. The present embodiment is applied in the case where there is little leakage of light leakage components to other floating diffusion layers other than the specific floating diffusion layer.

Figure 23:
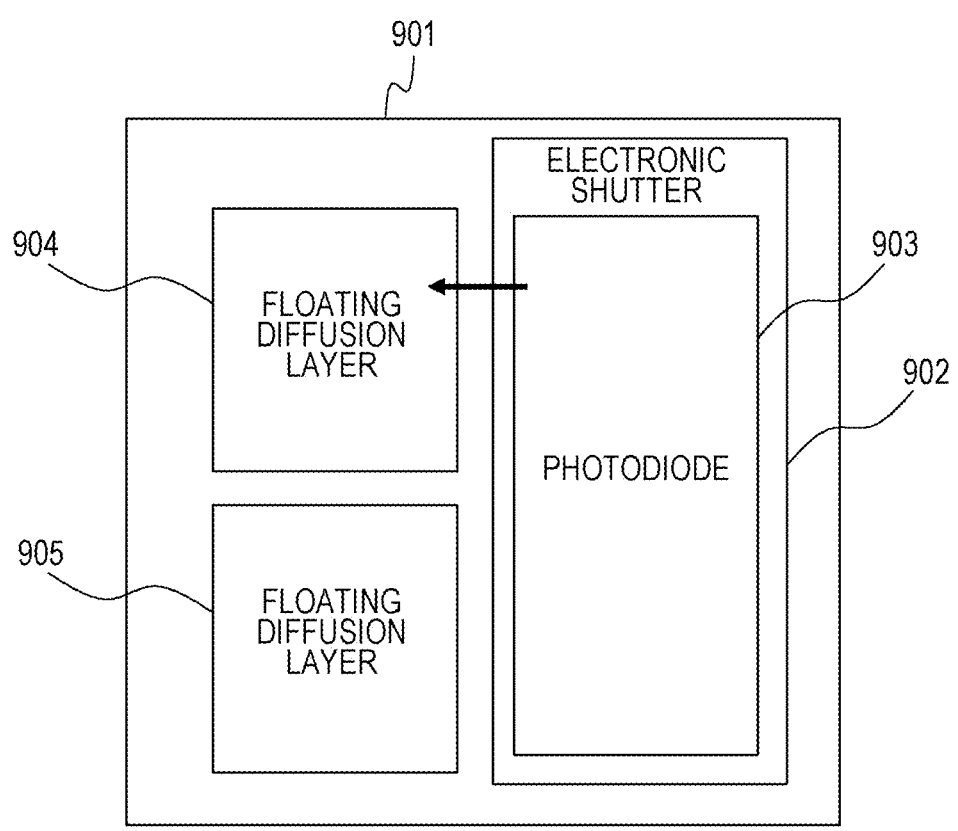
FIG. 23 is a drawing depicting a configuration of a pixel of a CCD-type image sensor in embodiment 7.

FIG. 23 depicts an overview of a pixel 901 of the CCD-type image sensor 113. The pixel 901 is provided with: a photodiode 903 with which light that is incident on the CCD-type image sensor 113 is converted into signal charge; an electronic shutter 902; a floating diffusion layer 904; and a floating diffusion layer 905. It should be noted that a plurality of gate electrodes (not depicted) for vertical transfer of charge are included in each floating diffusion layer.

The electronic shutter 902 is arranged at the substrate side of the photodiode 903 (in the direction perpendicular to the page space). Furthermore, it is assumed that signals accumulated in the photodiode 903 pass to the substrate side by means of the electronic shutter 902. Alternatively, it is assumed that said signals pass to a floating diffusion layer in which the potential becomes low (the floating diffusion layer 904 in the drawing), in the case where signal charge inside a floating diffusion layer is to be output from the image sensor 113. The overall configuration of the imaging device 101 according to the present embodiment is the same as in FIG. 5; however, it should be noted that, for simplicity, a case is described in which light of one wavelength is used, with only the first light source 103 being used and the second light source 104 not being used.

Figure 24:
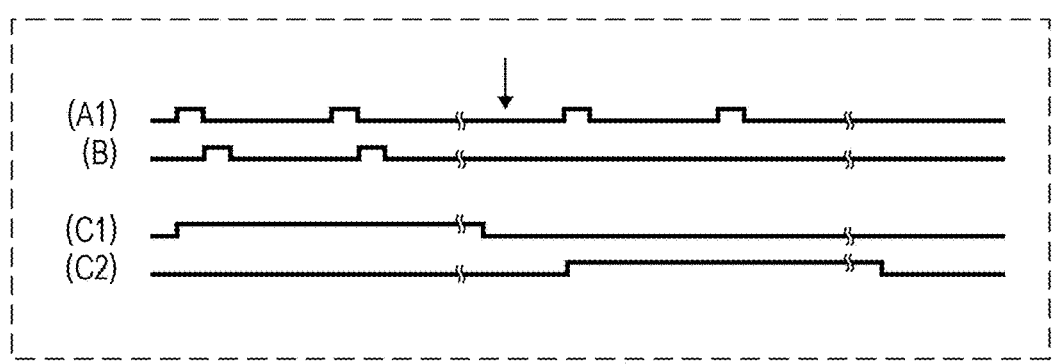
FIG. 24 is a timing chart depicting an operation in embodiment 7.

FIG. 24 is a timing chart depicting an operation in the present embodiment. Signal A1 indicates the waveform of pulsed light emitted from the first light source 103, signal B indicates the opening and closing timings of the electronic shutter 902, and signals C1 and C2 respectively indicate the on/off timings of the floating diffusion layers 904 and 905.

The floating diffusion layer 904 detects components that have scattered inside the living body, from within the pulsed light radiated onto the living body. At such time, the potential of the floating diffusion layer 904 is set to be relatively compared to that of the floating diffusion layer 905. Therefore, most of the light leakage components leak into the floating diffusion layer 904, and the light leakage components that leak into the floating diffusion layer 905 are so little that they can be ignored.

Next, at the time indicated by the arrow in FIG. 24, the signal charge accumulated in the floating diffusion layer 904 is vertically transferred to another floating diffusion layer that is not depicted, and the signal charge accumulated in the floating diffusion layer 905 is vertically transferred to the floating diffusion layer 904. In other words, the signal charge accumulated in the floating diffusion layers is shifted one by one. Thus, it appears as if the physical position of the floating diffusion layer 905 has moved to the position of the floating diffusion layer 904, and therefore the floating diffusion layer 904 is treated virtually as the floating diffusion layer 905. At such time, in the floating diffusion layer 904, in order to detect the light leakage component, a reading transfer state is maintained (a state in which the potential is lowered compared to that of the other floating diffusion layers), and the closed state of the electronic shutter is maintained. Thus, although only the light leakage component is detected in the floating diffusion layer 904, because the floating diffusion layer 904 is treated virtually as the floating diffusion layer 905, the imaging device 101 perceives the floating diffusion layer 905 as having detected only the light leakage component.

At such time, in the same manner as in embodiment 4, background light can also be acquired at the same time by opening the electronic shutter after a sufficient period of time has elapsed from the pulsed light reaching the image sensor.

By implementing this kind of driving, one floating diffusion layer detects components that have scattered inside the living body and light leakage components, and another floating diffusion layer detects light leakage components and background light components. It is possible for the components that have scattered inside the living body to be accurately obtained by subjecting these components detected by different floating diffusion layers to subtraction processing.

What is claimed is:

1. An imaging device for capturing an image of a target object, comprising:
   a first light source that, in operation, emits pulsed light that is radiated onto the target object;
   an image sensor that includes pixels, each of the pixels including
   photoelectric converter that, in operation, converts incident light into signal charge,
   a first accumulator that, in operation, accumulates the signal charge,
   a second accumulator that, in operation, accumulates the signal charge, and a discharger that, in operation, discharges the signal charge; and a controller that, in operation, controls the first light source and the image sensor, wherein the controller, in a first frame period that is a period in which the image of one frame is captured,
causes the first light source to emit the pulsed light,
in a first period that includes a period in which, from within the pulsed light, a surface reflected component reflected by a surface of the target object is incident on the image sensor,
causes the first accumulator and the second accumulator to accumulate, from within the signal charge, a portion that has not been discharged to the discharger, by setting a state of the image sensor to a state in which the signal charge is discharged to the discharger,
in a second period in which, from within the pulsed light, an internally scattered component that has scattered inside the target object is incident on the image sensor,
causes the first accumulator to accumulate the signal charge by setting the state of the image sensor to a state in which the signal charge is not discharged to the discharger and the signal charge is accumulated in the first accumulator, and,
after the first period and the second period, causes the image sensor to generate a first signal that is based on the signal charge accumulated in the first accumulator, and a second signal that is based on the signal charge accumulated in the second accumulator.

2. The imaging device according to claim 1, further comprising a signal processor that is electrically connected to the image sensor,
wherein, in operation, the signal processor generates a signal indicating the image, by performing a calculation using the first signal and the second signal, for each of the pixels.

3. The imaging device according to claim 2,
wherein, in operation, the signal processor generates the signal indicating the image, by subtracting the second signal from the first signal, for each of the pixels.

4. The imaging device according to claim 1,
wherein the controller,
in a second frame period that is different from the first frame period,
causes the first light source to emit the pulsed light,
in a third period that includes a period in which, from within the pulsed light, the surface reflected component is incident on the image sensor,
causes the first accumulator and the second accumulator to accumulate, from within the signal charge, the portion that has not been discharged to the discharger, by setting the state of the image sensor to the state in which the signal charge is discharged to the discharger, and,
after the third period, causes the image sensor to generate a third signal that is based on the signal charge accumulated in the first accumulator, and a fourth signal that is based on the signal charge accumulated in the second accumulator.

5. The imaging device according to claim 4, further comprising a signal processor that is electrically connected to the image sensor,
wherein, in operation, the signal processor generates a signal indicating the image, by performing a calculation using the first signal, the second signal, the third signal, and the fourth signal, for each of the pixels.

6. The imaging device according to claim 5,
wherein, when the first signal is S1, the second signal is S2, the third signal is S3, and the fourth signal is S4,
the signal processor, in operation, generates a signal S obtained by the calculation S=S1−S2×S3/S4, as the signal indicating the image.

7. The imaging device according to claim 1,
wherein the controller,
in a second frame period that is different from the first frame period,
causes the first light source to emit the pulsed light,
in a third period that includes a period in which, from within the pulsed light, the surface reflected component is incident on the image sensor,
causes the first accumulator and the second accumulator to accumulate, from within the signal charge, the portion that has not been discharged to the discharger, by setting the state of the image sensor to the state in which the signal charge is discharged to the discharger,
in a fourth period in which, from within the pulsed light, the internally scattered component is incident on the image sensor,
causes the second accumulator to accumulate the signal charge by setting the state of the image sensor to a state in which the signal charge is not discharged to the discharger and the signal charge is accumulated in the second accumulator, and,
after the third period and the fourth period, causes the image sensor to generate a third signal that is based on the signal charge accumulated in the first accumulator, and a fourth signal that is based on the signal charge accumulated in the second accumulator.

8. The imaging device according to claim 7, further comprising a signal processor that is electrically connected to the image sensor,
wherein, in operation, the signal processor generates a signal indicating the image in the second frame period, by subtracting a signal obtained by multiplying the third signal by a coefficient, from the fourth signal, for each of the pixels.

9. The imaging device according to claim 8,
wherein, in operation, the signal processor detects motion of the target object on the basis of the signal indicating the image, for each of the pixels, and
changes the coefficient using at least one of the first to fourth signals, for a pixel in which no motion of the target object is detected, from among the pixels.

10. The imaging device according to claim 1,
wherein the controller, in the first frame period,
in a period in which the pulsed light is not incident on the image sensor,
causes the second accumulator to further accumulate the signal charge, by setting the state of the image sensor to a state in which the signal charge is not discharged to the discharger and the signal charge is accumulated in the second accumulator.

11. The imaging device according to claim 1,
wherein the first light source, in operation, emits first pulsed light and second pulsed light that is emitted after the first pulsed light, each of the first pulsed light and the second pulsed light being the pulsed light, and
the controller, after incidence of the first pulsed light onto the image sensor has ended, before incidence of the second pulsed light onto the image sensor starts, causes the second accumulator to further accumulate the signal charge, by setting the state of the image sensor to a state in which the signal charge is not discharged to the discharger and the signal charge is accumulated in the second accumulator.

12. The imaging device according to claim 1,
wherein the controller, in the first frame period,
after accumulation of signal charge caused by the pulsed light in the first and second accumulators has completed,
causes the second accumulator to further accumulate the signal charge, by setting the state of the image sensor to a state in which the signal charge is not discharged to the discharger and the signal charge is accumulated in the second accumulator.

13. The imaging device according to claim 1,
further comprising a second light source that, in operation, emits third pulsed light that has a different wavelength from a wavelength of the pulsed light from the first light source,
wherein the image sensor further includes a third accumulator that, in operation, accumulates the signal charge, and
the controller, in the first frame period,
after the first period and the second period,
causes the second light source to emit the third pulsed light,
in a fifth period that includes a period in which, from within the third pulsed light, the surface reflected component is incident on the image sensor,
causes the first accumulator, the second accumulator, and the third accumulator to accumulate, from within the signal charge, the portion that has not been discharged to the discharger, by setting the state of the image sensor to the state in which the signal charge is discharged to the discharger,
in a sixth period in which, from within the third pulsed light, the internally scattered component is incident on the image sensor,
causes the third accumulator to accumulate the signal charge, by setting the state of the image sensor to a state in which the signal charge is not discharged to the discharger and the signal charge is accumulated in the third accumulator, and,
after the fifth period and the sixth period, causes the image sensor to generate the first signal that is based on the signal charge accumulated in the first accumulator, the second signal that is based on the signal charge accumulated in the second accumulator, and a third signal that is based on the signal charge accumulated in the third accumulator.

* * * * *